(12) United States Patent
Djupesland et al.

(10) Patent No.: US 11,602,603 B2
(45) Date of Patent: Mar. 14, 2023

(54) NASAL DELIVERY DEVICES

(71) Applicant: OptiNose AS, Oslo (NO)

(72) Inventors: Per Gisle Djupesland, Oslo (NO);
Colin David Sheldrake, Wiltshire (GB)

(73) Assignee: OptiNose, Inc., Yardley, PA (US)

( * ) Notice: Subject to any disclaimer, the term of this patent is extended or adjusted under 35 U.S.C. 154(b) by 24 days.

(21) Appl. No.: 17/305,260

(22) Filed: Jul. 2, 2021

(65) Prior Publication Data

US 2022/0031980 A1 Feb. 3, 2022

Related U.S. Application Data

(63) Continuation of application No. 16/285,694, filed on Feb. 26, 2019, now Pat. No. 11,083,858, which is a (Continued)

(30) Foreign Application Priority Data

Oct. 3, 2007 (GB) .................................... 0719299
Apr. 15, 2008 (GB) .................................... 0806808

(51) Int. Cl.
*A61M 15/08* (2006.01)
*A61M 15/00* (2006.01)
(Continued)

(52) U.S. Cl.
CPC .......... *A61M 15/08* (2013.01); *A61M 11/006* (2014.02); *A61M 11/007* (2014.02);
(Continued)

(58) Field of Classification Search
CPC ........ A61M 11/00; A61M 11/006–007; A61M 11/02; A61M 11/08; A61M 15/00;
(Continued)

(56) References Cited

U.S. PATENT DOCUMENTS 605,436 A 6/1898 Kellogg
642,748 A 2/1900 Manners
(Continued)

FOREIGN PATENT DOCUMENTS

DE 30 40 641 A1 5/1982
DE 298 18 662 U1 4/2000
(Continued)

OTHER PUBLICATIONS

English Language Translation of DE 30 40 641 A1.
(Continued)

*Primary Examiner* — Rachel T Sippel
(74) *Attorney, Agent, or Firm* — Finnegan, Henderson, Farabow, Garrett & Dunner, LLP

(57) ABSTRACT

A nasal delivery device for and a method of delivering substance to a nasal airway of a subject, the nasal delivery device comprising: a mouthpiece (519) through which the subject in use exhales to cause closure of the oropharyngeal velum of the subject; a nosepiece (517) for fitting to a nostril of a subject, the nosepiece including a nozzle (549) through which substance is in use delivered to the nasal airway; and a manually-actuatable substance supply unit (520) for delivering substance through the nozzle of the nosepiece.

25 Claims, 33 Drawing Sheets

Related U.S. Application Data continuation of application No. 14/721,097, filed on May 26, 2015, now Pat. No. 10,252,010, which is a continuation of application No. 12/681,150, filed as application No. PCT/GB2008/003377 on Oct. 3, 2008, now Pat. No. 9,067,034.

(51) Int. Cl.
  *A61M 11/00* (2006.01)
  *A61M 11/02* (2006.01)
  *A61M 11/08* (2006.01)

(52) U.S. Cl.
  CPC .......... *A61M 11/02* (2013.01); *A61M 15/002* (2014.02); *A61M 15/0003* (2014.02); *A61M 15/009* (2013.01); *A61M 15/0015* (2014.02); *A61M 15/0021* (2014.02); *A61M 15/0098* (2014.02); *A61M 11/08* (2013.01); *A61M 15/0095* (2014.02); *A61M 2202/0468* (2013.01); *A61M 2202/064* (2013.01); *A61M 2205/8281* (2013.01)

(58) Field of Classification Search
  CPC .............. A61M 15/08; A61M 15/0003; A61M 15/0015; A61M 15/002; A61M 15/0021; A61M 15/0098; A61M 15/009; A61M 15/0095; A61M 2205/8281
  See application file for complete search history.

(56) References Cited

U.S. PATENT DOCUMENTS

| | | |
|---|---|---|
| 658,436 A | 9/1900 | Groth |
| 746,749 A | 12/1903 | Seidel |
| 794,641 A | 7/1905 | Ramey |
| 902,832 A | 11/1908 | Philbrook |
| 2,470,297 A | 5/1949 | Fields |
| 5,355,873 A | 10/1994 | Del Bon et al. |
| 5,797,392 A | 8/1998 | Keldmann et al. |
| 6,397,839 B1 | 6/2002 | Stradella |
| 6,648,848 B1 | 11/2003 | Keldmann et al. |
| 6,715,485 B1 | 4/2004 | Djupesland |
| D530,815 S | 10/2006 | Murphy et al. |
| 7,347,201 B2 | 3/2008 | Djupesland |
| 7,377,901 B2 | 5/2008 | Djupesland et al. |
| 7,481,218 B2 | 1/2009 | Djupesland |
| 7,543,581 B2 | 6/2009 | Djupesland |
| 7,740,014 B2 | 6/2010 | Djupesland |
| 7,784,460 B2 | 8/2010 | Djupesland et al. |
| 7,841,337 B2 | 11/2010 | Djupesland |
| 7,854,227 B2 | 12/2010 | Djupesland |
| 7,934,503 B2 | 5/2011 | Djupesland et al. |
| 7,975,690 B2 | 7/2011 | Djupesland |
| 8,047,202 B2 | 11/2011 | Djupesland |
| 8,146,589 B2 | 4/2012 | Djupesland |
| 8,171,929 B2 | 5/2012 | Djupesland et al. |
| 8,327,844 B2 | 12/2012 | Djupesland |
| 8,511,303 B2 | 8/2013 | Djupesland |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,590,530 B2 | 11/2013 | Djupesland et al. |
| 8,596,278 B2 | 12/2013 | Djupesland |
| 8,800,555 B2 | 8/2014 | Djupesland |
| 8,875,704 B2 | 11/2014 | Djupesland et al. |
| 8,899,229 B2 | 12/2014 | Djupesland et al. |
| 8,910,629 B2 | 12/2014 | Djupesland et al. |
| D723,156 S | 2/2015 | Djupesland et al. |
| D725,769 S | 3/2015 | Djupesland et al. |
| 8,978,647 B2 | 3/2015 | Djupesland et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,108,015 B2 | 8/2015 | Djupesland |
| 9,119,932 B2 | 9/2015 | Djupesland |
| 9,132,249 B2 | 9/2015 | Djupesland |
| 9,144,652 B2 | 9/2015 | Djupesland et al. |
| 9,168,341 B2 | 10/2015 | Djupesland |
| 9,205,208 B2 | 12/2015 | Djupesland |
| 9,205,209 B2 | 12/2015 | Djupesland |
| 9,272,104 B2 | 3/2016 | Djupesland |
| D759,805 S | 6/2016 | Djupesland |
| D761,951 S | 7/2016 | Djupesland |
| 9,452,272 B2 | 9/2016 | Djupesland et al. |
| 9,468,727 B2 | 10/2016 | Djupesland |
| D773,644 S | 12/2016 | Djupesland |
| 9,522,243 B2 | 12/2016 | Djupesland |
| 9,566,402 B2 | 2/2017 | Djupesland |
| 9,649,456 B2 | 5/2017 | Djupesland et al. |
| D809,128 S | 1/2018 | Djupesland |
| 10,252,010 B2 | 4/2019 | Djupesland et al. |
| 2004/0024330 A1 | 2/2004 | Djupesland et al. |
| 2004/0112378 A1 | 6/2004 | Djupesland |
| 2004/0112379 A1 | 6/2004 | Djupesland |
| 2004/0112380 A1 | 6/2004 | Djupesland |
| 2004/0149289 A1 | 8/2004 | Djupesland |
| 2004/0182388 A1 | 9/2004 | Djupesland |
| 2005/0028812 A1 | 2/2005 | Djupesland |
| 2005/0072430 A1 | 4/2005 | Djupesland |
| 2005/0235992 A1 | 10/2005 | Djupesland |
| 2006/0096589 A1 | 5/2006 | Djupesland |
| 2006/0107957 A1 | 5/2006 | Djupesland |
| 2006/0169278 A1 | 8/2006 | Djupesland et al. |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2006/0289007 A1 | 12/2006 | Williams et al. |
| 2007/0039614 A1 | 2/2007 | Djupesland |
| 2007/0125371 A1 | 6/2007 | Djupesland |
| 2007/0186927 A1 | 8/2007 | Djupesland et al. |
| 2008/0161771 A1 | 7/2008 | Djupesland |
| 2008/0163874 A1 | 7/2008 | Djupesland |
| 2008/0221471 A1 | 9/2008 | Djupesland et al. |
| 2008/0223363 A1 | 9/2008 | Djupesland |
| 2008/0289629 A1 | 11/2008 | Djupesland et al. |
| 2009/0101146 A1 | 4/2009 | Djupesland |
| 2009/0293873 A1 | 12/2009 | Djupesland et al. |
| 2009/0304802 A1 | 12/2009 | Djupesland et al. |
| 2009/0314293 A1 | 12/2009 | Djupesland |
| 2009/0320832 A1 | 12/2009 | Djupesland |
| 2010/0035805 A1 | 2/2010 | Hafner |
| 2010/0051022 A1 | 3/2010 | Djupesland et al. |
| 2010/0057047 A1 | 3/2010 | Djupesland et al. |
| 2010/0199984 A1 | 8/2010 | Williams et al. |
| 2010/0242959 A1 | 9/2010 | Djupesland et al. |
| 2010/0282246 A1 | 11/2010 | Djupesland et al. |
| 2010/0288275 A1 | 11/2010 | Djupesland et al. |
| 2010/0300439 A1 | 12/2010 | Djupesland et al. |
| 2011/0023869 A1 | 2/2011 | Djupesland |
| 2011/0053827 A1 | 3/2011 | Hafner |
| 2011/0088690 A1 | 4/2011 | Djupesland et al. |
| 2011/0088691 A1 | 4/2011 | Djupesland |
| 2011/0114087 A1 | 5/2011 | Djupesland et al. |
| 2011/0120456 A1 | 5/2011 | Immel |
| 2011/0126830 A1 | 6/2011 | Djupesland et al. |
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |
| 2014/0060536 A1 | 3/2014 | Djupesland |
| 2014/0073562 A1 | 3/2014 | Djupesland et al. |
| 2014/0144442 A1 | 5/2014 | Djupesland et al. |

(56) References Cited

U.S. PATENT DOCUMENTS

| | | | |
|---|---|---|---|
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0095989 A1 | 4/2016 | Djupesland |
| 2016/0095993 A1 | 4/2016 | Djupesland |
| 2016/0101249 A1 | 4/2016 | Djupesland |
| 2016/0166788 A1 | 6/2016 | Djupesland et al. |
| 2016/0184537 A1 | 6/2016 | Djupesland |
| 2016/0193435 A1 | 7/2016 | Djupesland |
| 2016/0250408 A1 | 9/2016 | Djupesland |
| 2016/0263334 A1 | 9/2016 | Djupesland |
| 2016/0279357 A1 | 9/2016 | Djupesland |
| 2016/0310683 A1 | 10/2016 | Djupesland et al. |
| 2016/0331916 A1 | 11/2016 | Djupesland et al. |
| 2016/0367771 A1 | 12/2016 | Djupesland |
| 2016/0367772 A1 | 12/2016 | Djupesland |
| 2016/0367774 A1 | 12/2016 | Djupesland et al. |
| 2017/0043108 A1 | 2/2017 | Djupesland et al. |
| 2017/0151397 A1 | 6/2017 | Djupesland |
| 2017/0203061 A1 | 7/2017 | Djupesland et al. |
| 2017/0216540 A1 | 8/2017 | Djupesland |
| 2017/0274164 A1 | 9/2017 | Djupesland et al. |
| 2017/0333649 A1 | 11/2017 | Djupesland |

FOREIGN PATENT DOCUMENTS

| | | |
|---|---|---|
| GB | 2 381 460 A | 5/2003 |
| GB | 2 395 909 A | 6/2004 |
| GB | 2 403 154 A | 12/2004 |
| GB | 2 404 867 A | 2/2005 |
| GB | 2 405 350 A | 3/2005 |
| GB | 2414414 A | 11/2005 |
| GB | 2418 147 A | 3/2006 |
| GB | 2 435 613 A | 9/2007 |
| JP | 62-097564 A | 5/1987 |
| JP | 2004-528073 A | 9/2004 |
| JP | 2005-500877 A | 1/2005 |
| JP | 2005-510261 A | 4/2005 |
| RU | 2004 100 276 A | 2/2005 |
| RU | 2 258 538 C2 | 8/2005 |
| WO | WO 95/11715 | 5/1995 |
| WO | WO 96/22802 | 8/1996 |
| WO | WO 98/53869 | 12/1998 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 02/074372 A2 | 9/2002 |
| WO | WO 02/083230 A1 | 10/2002 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/0441 72 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |
| WO | WO 2020/070321 | 4/2020 |

OTHER PUBLICATIONS

English Language Translation of JP 62-097564 A.
English Language Translation of DE 298 18 662 U1.
Cindy H. Dubin, *Nothing to Sneeze At*, Pharmaceutical Formulation & Quality Magazine (Jan. 29, 2003).
Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, Bi-directional Nasal Drug Delivery, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
G. Furness, *Nasal Drug Delivery: Rapid Onset Via A Convenient Route*, ONdrugDelivery Ltd. (2005).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be An Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using A Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).

(56) References Cited

OTHER PUBLICATIONS

Vlckovia et al., *Effective Treatment Of Mild-to-Moderate Nasal Polyposis with Fluticasone Delivered By A Novel Device*, Rhinology (Oct. 22, 2009).

Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).

F.S. Hansen et al., *Preliminary Efficacy of Fluticasone Delivered By a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).

Stewart J. Tepper, *Clinical Implications for Breath-Powered Powder Sumatriptan Intranasal Treatment*, Headache, The American Headache Society (Apr. 29, 2013).

Mohammad Obaidi et al., *Improved Pharmacokinetics of Sumatriptan With Breath Powered Nasal Delivery of Sumatriptan Powder*, Headache, The American Headache Society (May 24, 2013).

Per Gisle Djupesland, *Breath Powdered Nasal Delivery: A New Route to Rapid Headache Relief*, Headache, The American Headache Society (Jun. 4, 2013).

Per Gisle Djupesland et al., *The Nasal Approach to Delivering Treatment for Brain Diseases: An Anatomic, Physiologic, and Delivery Technology Overview*, Therapeutic Delivery (2014).

R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sept. 8, 2014).

S.J. Tepper et al., *A VP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).

D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).

R. Mahmoud, *Breathe Out*, Innovations in Phar, Tech. (Dec. 10, 2015).

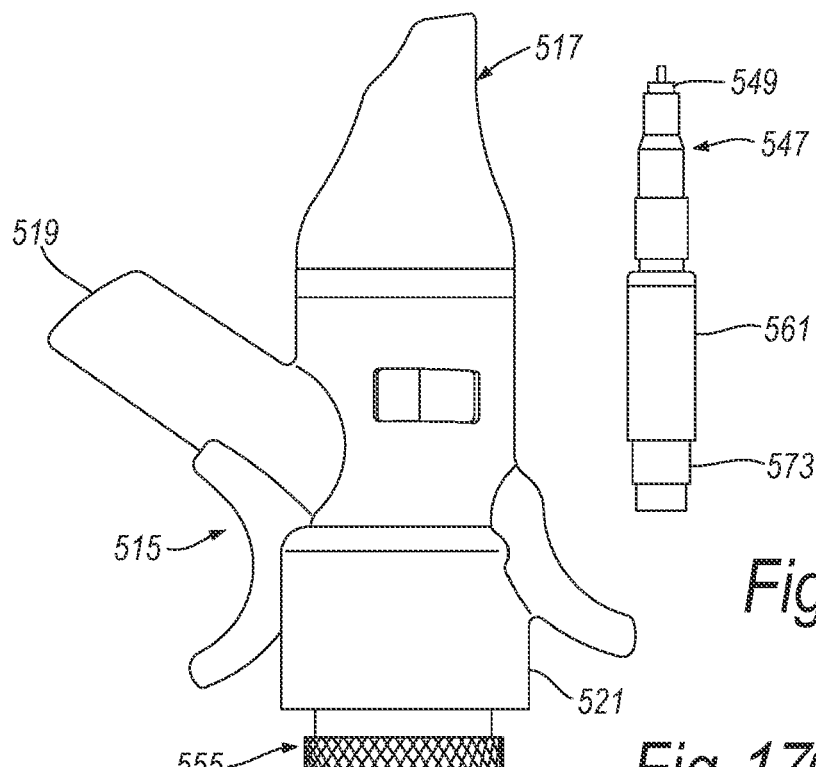
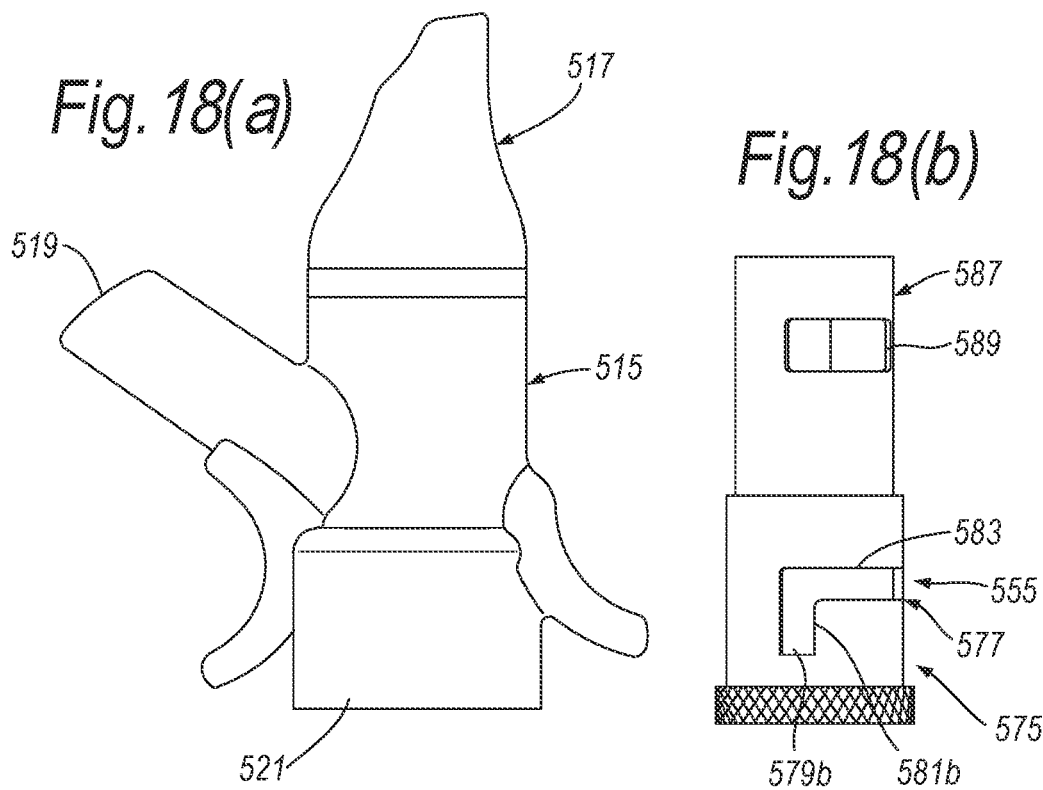

NASAL DELIVERY DEVICES

This application is a continuation application of U.S. application Ser. No. 16/285,694, filed on Feb. 26, 2019, which is a continuation application of U.S. application Ser. No. 14/721,097, filed on May 26, 2015, now U.S. Pat. No. 10,252,010, which is a continuation application of U.S. application Ser. No. 12/681,150, filed on Dec. 21, 2010, now U.S. Pat. No. 9,067,034, which is a U.S. national phase application of International Application No. PCT/GB2008/03377, filed on Oct. 3, 2008, which claims priority to GB0806808.2, filed on Apr. 15, 2008 and to GB0719299.0, filed on Oct. 3, 2007. The disclosure of each of the above applications is incorporated herein by reference in its entirety.

The present invention relates to a nasal delivery device for and a method of delivering a substance, in particular one of a liquid, as a suspension or solution, or a powder containing a medicament, especially systemic or topical pharmaceuticals, or a vaccine to the nasal airway of a subject.

Referring to FIG. 40, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as *Helicobacter pylori* infections which cause gastric ulcers.

WO-A-2000/051672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

It is an aim of the present invention to provide nasal delivery devices and nasal delivery methods for providing for delivery of a substance to a nasal cavity of subject, and in particular relatively-simple mechanically-actuatable delivery devices.

In one aspect the present invention provides a nasal delivery device for delivering substance to a nasal airway of a subject, comprising: a mouthpiece through which the subject in use exhales to cause closure of the oropharyngeal velum of the subject; a nosepiece for fitting to a nostril of a subject, the nosepiece including a nozzle through which substance is in use delivered to the nasal airway; and a manually-actuatable substance supply unit for delivering substance through the nozzle of the nosepiece.

In one embodiment the delivery device comprises: a latch mechanism which is operative between a first, inoperative configuration in which the substance supply unit is inactuatable and a second, operative configuration in which the substance supply unit is actuatable.

In one embodiment the latch mechanism is a breath-operated mechanism which comprises a latch member which is movable on exhalation by the subject between a first, inoperative position in which the substance supply unit is inactuatable and a second, operative position in which the substance supply unit is actuatable.

In one embodiment the latch mechanism comprises a biasing element for biasing the latch member to the inoperative position.

In one embodiment the latch mechanism comprises an operative element which is coupled to the latch member and operated by the exhalation breath of the subject to move the latch member to the operative position.

In one embodiment the operative element comprises an inflatable element which is expanded on exhalation by the subject.

In one embodiment the delivery device further comprises: a valve assembly which is fluidly connected to the mouthpiece and the nosepiece, and operable between a closed configuration in which there is no fluid communication path between the mouthpiece and the nosepiece and an open configuration on actuation of the substance supply unit, such as to provide for an air flow through the nosepiece on actuation of the substance supply unit.

In one embodiment the delivery device further comprises: a flow channel fluidly connecting the nosepiece and the mouthpiece unit, whereby exhaled air from an exhalation breath is delivered through the nosepiece.

In one embodiment the substance supply unit is configured to be manually depressed by the subject.

In another embodiment the delivery device further comprises: a loading mechanism which is operable to be primed with a loading force and manually actuated to apply the loading force to the substance supply unit, such as to actuate the same.

In one embodiment the substance supply unit comprises a substance-containing chamber which provides a volume of substance for delivery by the delivery device.

In one embodiment the substance supply unit further comprises a piston member which is movable relative to the substance-containing chamber to deliver a dose of substance from the substance-containing chamber.

In one embodiment the piston member is movable between a plurality of respective positions, such as to deliver a metered dose of substance with each advance of the piston member between respective ones of the positions.

In one embodiment the piston member is movable relative to a body member and one of the piston member and the body member includes a track which includes track sections which define each of the respective positions, and the other of the piston member and the body member includes a follower which is located in the track and moved in succession to each of the respective positions on actuation of the piston member.

In one embodiment the substance supply unit is a duo-dose pump unit, with the piston member being movable to two separate positions.

In one embodiment the substance-containing chamber comprises first and second chambers which each separately contain a respective substance component and provide for re-constitution of the substance components to provide a re-constituted substance for delivery by the delivery device.

In one embodiment the substance-containing chamber further comprises a frangible member which normally separates the first and second chambers and when ruptured provides for re-constitution of the substance components to provide a re-constituted substance for delivery by the delivery device.

In one embodiment the delivery device includes a rupturing element which is configured to rupture the frangible member on fitting the substance-containing chamber to the housing.

In one embodiment the substance supply unit provides for the delivery of a powder substance.

In another embodiment the substance supply unit provides for the delivery of a liquid substance.

In one embodiment the substance is delivered as an aerosol.

In another embodiment the substance is delivered as a jet.

In one embodiment the nosepiece includes a sealing member which provides for a tight sealing fit with the nostril of the subject.

In another aspect the present invention provides a method of delivering substance to a nasal airway of a subject, comprising the steps of: providing a delivery device which comprises a nosepiece for fitting to a nostril of a subject, the nosepiece including a nozzle through which substance is delivered, and a manually-actuatable substance supply unit for delivering substance through the nozzle of the nosepiece; fitting the nosepiece to a nostril of a subject; and manually actuating the substance supply unit to deliver substance to the nasal airway of the subject.

In one embodiment the nosepiece fitting step comprises the step of: fitting the nosepiece to a nostril of a subject, such that the nosepiece is in sealing engagement with the nostril of the subject.

In one embodiment the method further comprises the step of: closing the oropharyngeal velum of the subject.

In one embodiment the delivery device further comprises a mouthpiece, and the oropharyngeal velum closing step comprises the step of: the subject exhaling through the mouthpiece such as to close the oropharyngeal velum of the subject.

In one embodiment the delivery device comprises a valve assembly which is fluidly connected to the mouthpiece and the nosepiece, and operable between a closed configuration in which there is no fluid communication path between the mouthpiece and the nosepiece and an open configuration on actuation of the substance supply unit, whereby an exhalation air flow is delivered through the nosepiece on actuation of the substance supply unit.

In one embodiment the delivery device further comprises a latch mechanism which is operative between a first, inoperative configuration in which the substance supply unit is inactuatable and a second, operative configuration in which the substance supply unit is actuatable.

In one embodiment the latch mechanism is a breath-operated mechanism which comprises a latch member which is movable on exhalation by the subject between a first, inoperative position in which the substance supply unit is inactuatable and a second, operative position in which the substance supply unit is actuatable.

In one embodiment the latch mechanism comprises a biasing element for biasing the latch member to the inoperative position.

In one embodiment the latch mechanism comprises an operative element which is coupled to the latch member and operated by the exhalation breath of the subject to move the latch member to the operative position.

In one embodiment the operative element comprises an inflatable element which is expanded on exhalation by the subject.

In one embodiment the method further comprises the step of: re-constituting the substance from at least first and second substance components.

In a further aspect the present invention provides a nasal delivery device for delivering substance to a nasal airway of a subject, comprising: a nosepiece for fitting to a nostril of a subject, the nosepiece including a nozzle through which substance is in use delivered to the nasal airway; and a manually-actuatable substance supply unit for delivering substance through the nozzle of the nosepiece.

Preferred embodiments of the present invention will now be described hereinbelow by way of example only with reference to the accompanying drawings, in which:

FIGS. 17 to 22 illustrate a nasal delivery device in accordance with a sixth embodiment of the present invention;

Figure 38:
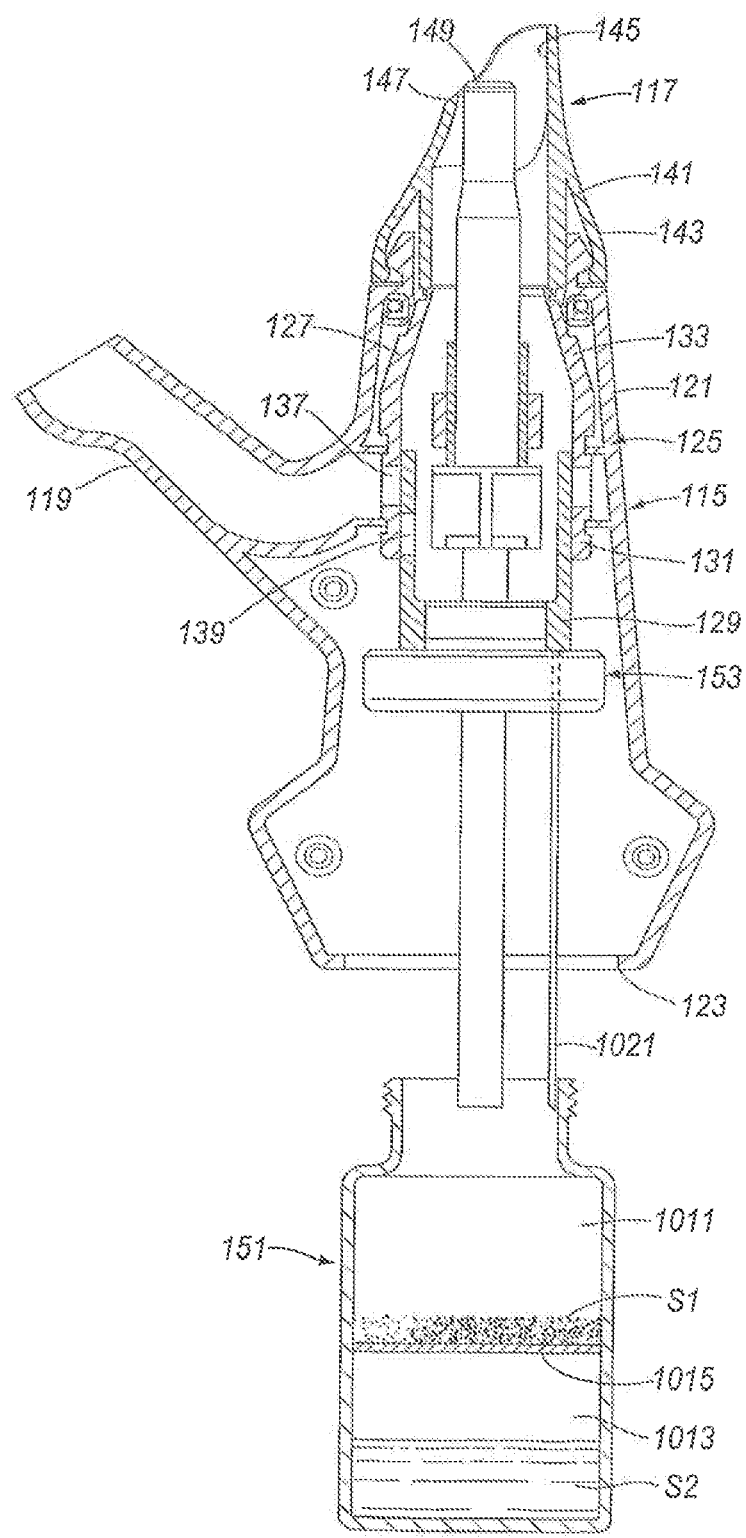
Figure 39:
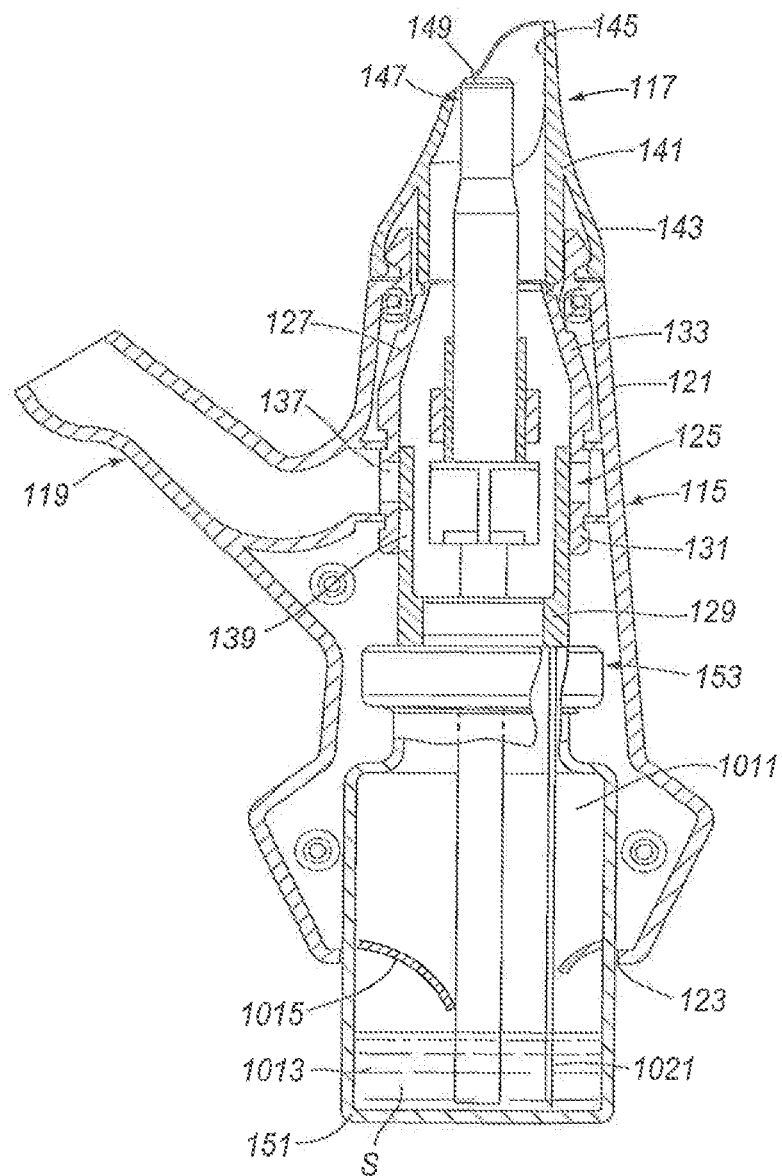
Figure 40:
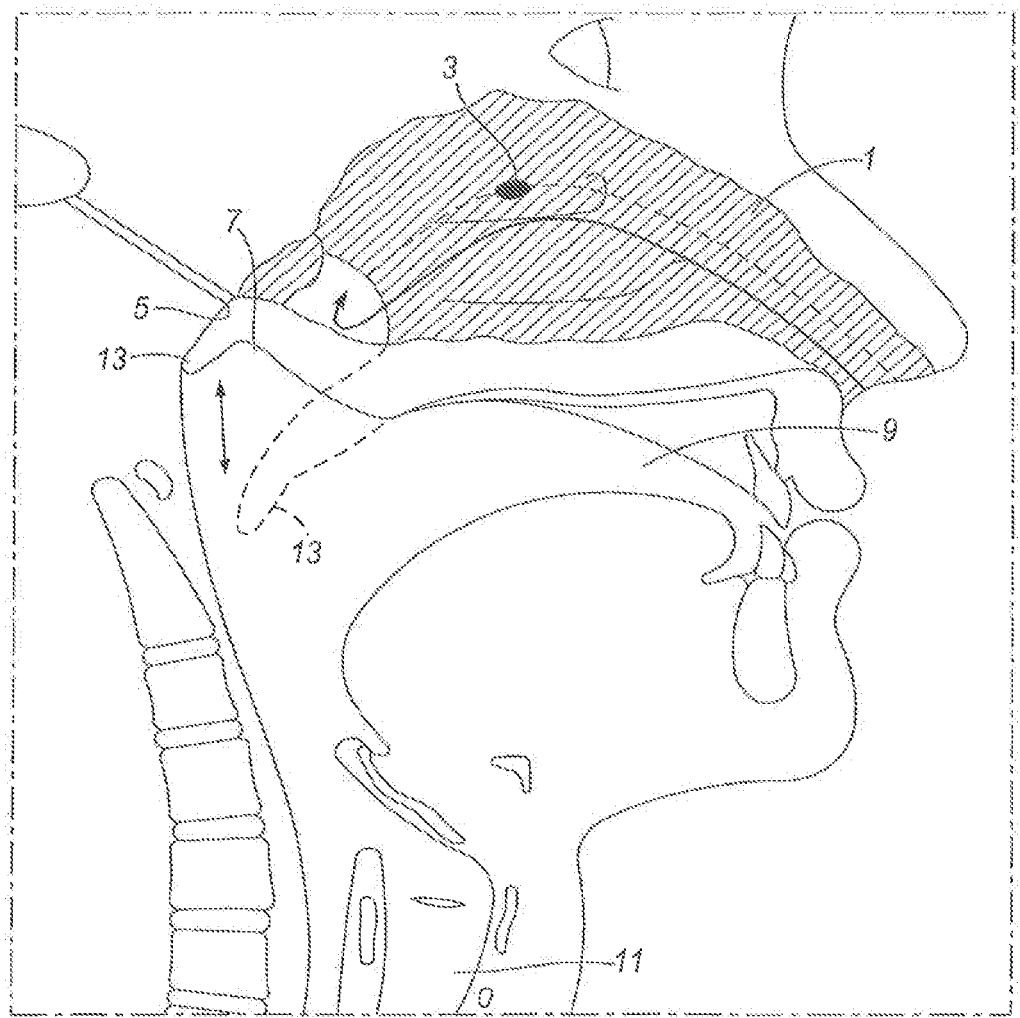

FIGS. 38 and 39 another embodiment of the present invention as a modification of the second-described embodiment; and FIG. 40 schematically illustrates the anatomy of the upper respiratory tract of a human subject.

Figure 1:
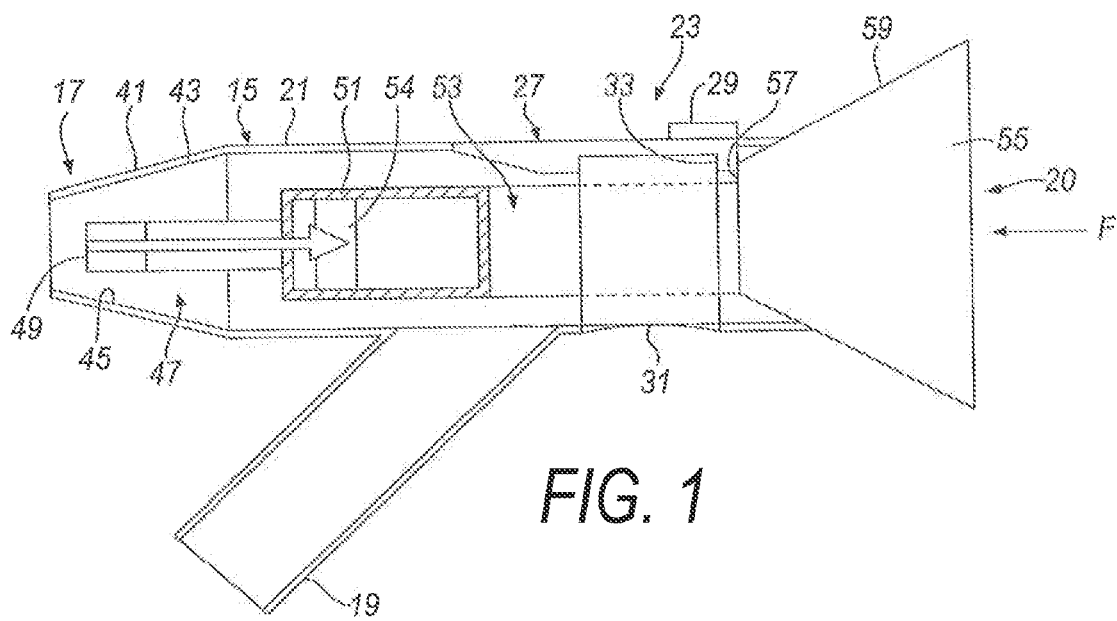
FIGS. 1 to 3 illustrate a nasal delivery device in accordance with a first embodiment of the present invention.
Figure 2:
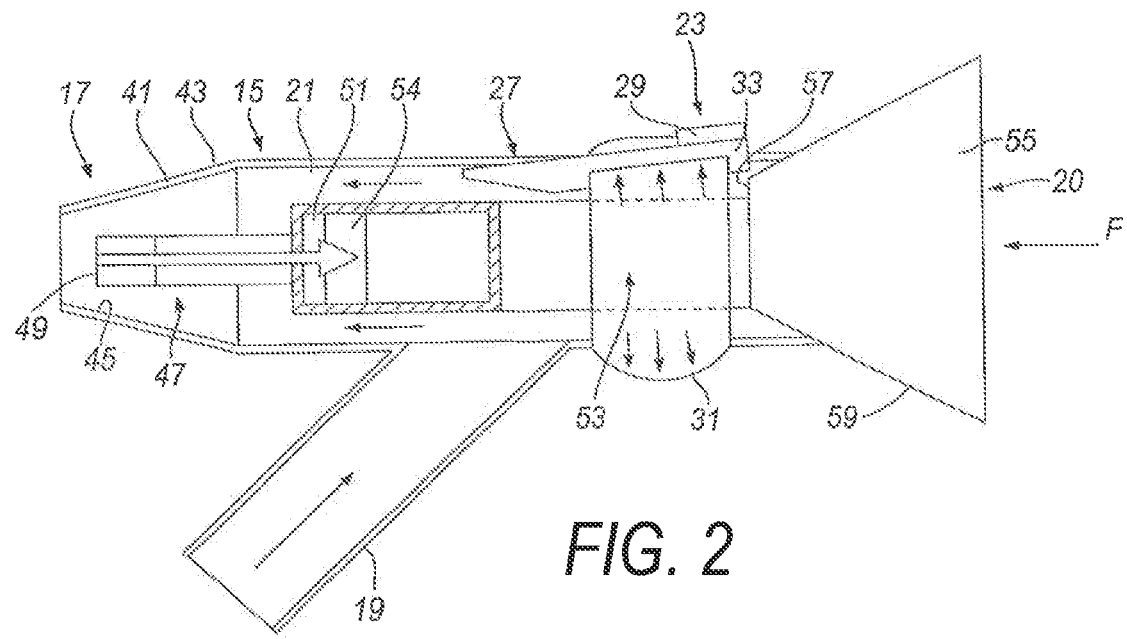
Figure 3:
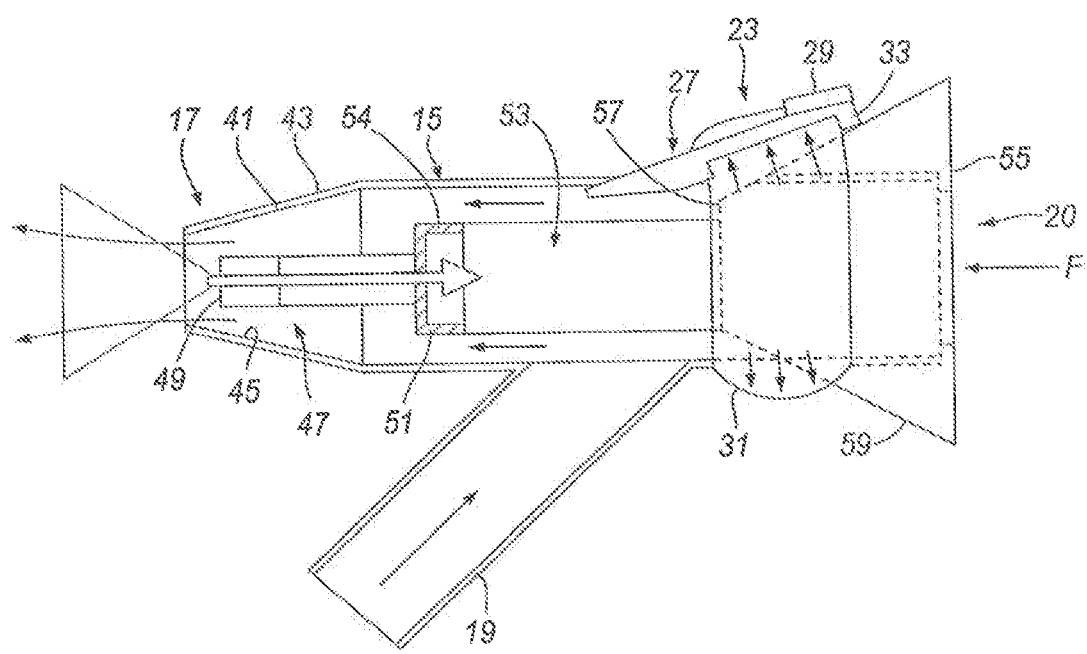
Figure 4:
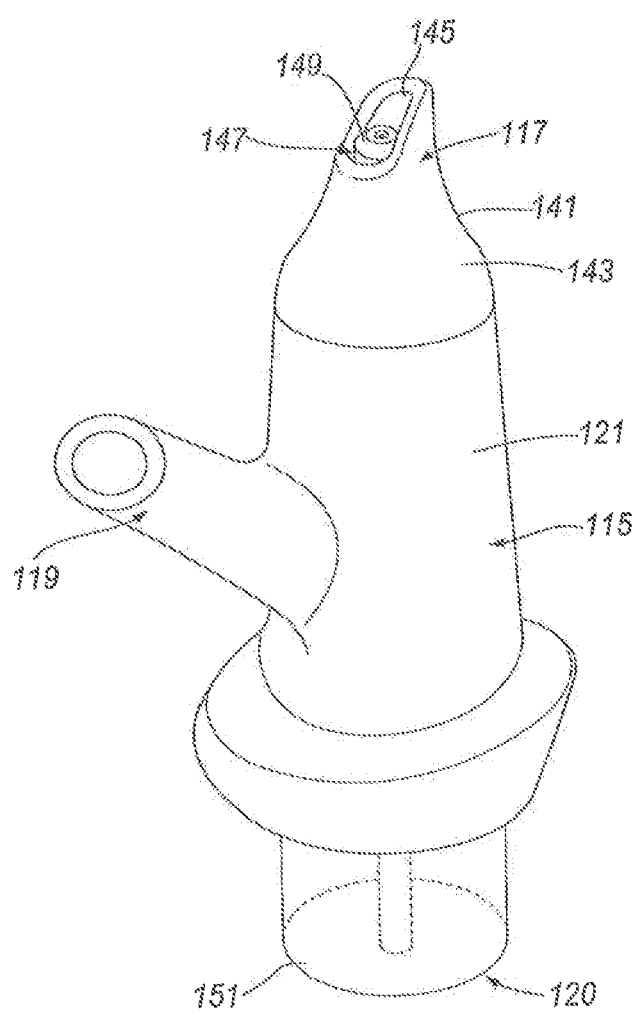
FIGS. 4 to 7 illustrate a nasal delivery device in accordance with a second embodiment of the present invention.
Figure 5:
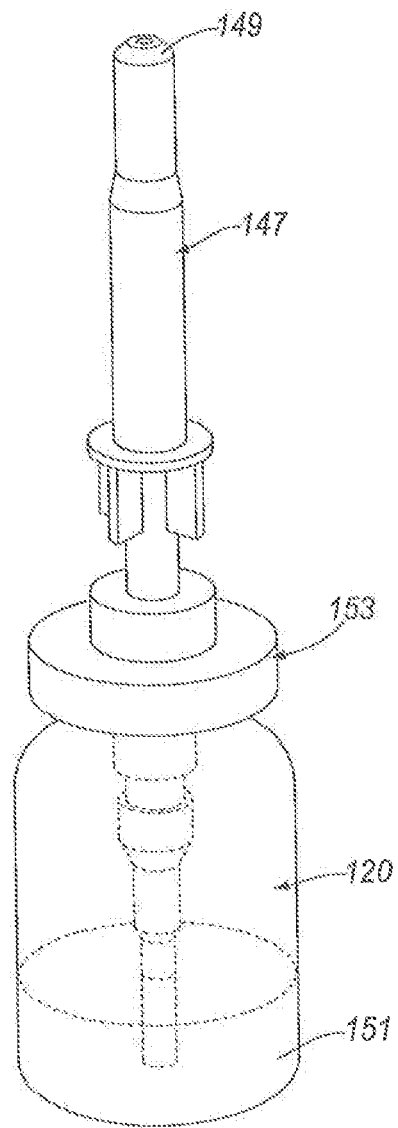

FIGS. 1 to 3 illustrate a manually-actuated, exhalation breath-operated nasal delivery device in accordance with a first embodiment of the present invention.

The delivery device comprises a housing 15, a nosepiece 17 for fitting in a nasal cavity of a subject, a mouthpiece 19 through which the subject in use exhales, and a substance supply unit 20, which is manually actuated to deliver substance to the nasal cavity of the subject.

The housing 15 comprises a body member 21, in this embodiment of elongate, tubular section, and a latch mechanism 23, which is operable between a closed, inoperative configuration, as illustrated in FIG. 1, in which the device is inoperative, and an open, operative configuration, as illustrated in FIG. 2, in which the substance supply unit 20 is actuatable.

The latch mechanism 23 comprises a latch member 27 which is movably coupled, in this embodiment hingeably-coupled, to the body member 21, a biasing element 29, in this embodiment a resilient element, which acts to bias the latch member 27 to a closed, inoperative position, in this embodiment an inner position, as illustrated in FIG. 1, and an operative element 31, which is operated by the exhalation breath of the subject to move the latch member 27 to an open, operative position, in this embodiment an outer position, against the bias of the biasing element 29, as illustrated in FIG. 2, which permits actuation of the substance supply unit 20.

In this embodiment the latch member 27 includes a detent 33, here a rearwardly-facing element, which acts to engage a counterpart detent 57 of the substance supply unit 20 and prevent actuation of the same when the latch member 27 is in the closed position, and is moved out of engagement with the counterpart detent 57 of the substance supply unit 20 to allow actuation of the same when the latch member 27 is in the open position.

In this embodiment the operative element 31 comprises an inflatable element, here a flexible, resilient element, which is expanded on exhalation by the subject into the mouthpiece 19, and operative to move the latch member 27 to the open position, which allows for actuation of the substance supply unit 20.

With this configuration, for so long as the subject is exhaling through the mouthpiece 19 sufficiently to displace the latch member 27 to the open position, the substance supply unit 20 is actuatable.

In this embodiment the operative element 31 is configured such as to require the generation of a predetermined pressure at the mouthpiece 19 to move the latch member 27 to the open position. In this way, closure of the velum of the subject is ensured prior to actuation of the substance supply unit 20.

The nosepiece 17 comprises a body member 41 which defines an outer guide surface 43, in this embodiment a frusto-conical element, for guiding the nosepiece 17 into a nasal cavity of the subject and an inner delivery channel 45, which is in fluid communication with the mouthpiece 19, such that an air flow is delivered into and through the nasal airway of the subject on exhalation by the subject through the mouthpiece 19, and an outlet unit 47 for delivering substance into the nasal airway of the subject, which is disposed within the delivery channel 45.

In this embodiment the outlet unit 47 comprises a nozzle 49 for delivering substance to the nasal airway of the subject. In this embodiment the nozzle 49 is disposed in the delivery channel 45 co-axially with the same. In this embodiment the nozzle 49 is configured to provide an aerosol spray. In an alternative embodiment, for the delivery of a liquid, the nozzle 49 could be configured to deliver a liquid jet as a column of liquid.

In a preferred embodiment the distal end of the outlet unit 47 is configured to extend at least about 2 cm, preferably at least about 3 cm, and more preferably from about 2 cm to about 3 cm, into the nasal cavity of the subject.

In this embodiment the substance supply unit 20 comprises a substance-containing chamber 51 which is fluidly connected to the outlet unit 47, and an actuator 53 which is operable to expel substance from the substance-containing chamber 51 to the outlet unit 47 and from the nozzle 49 thereof, in this embodiment as an aerosol spray.

In this embodiment the actuator 53 comprises a piston element 54, which is slideably disposed within the substance-containing chamber 51, and an actuating member 55, here in the form of button, which is coupled to the piston element 54 and manually operable, here depressed, by the subject, typically by a thumb or finger, in actuating the substance supply unit 20.

In this embodiment the actuating member 55 includes a detent 57, here a forwardly-facing surface, which is operable to engage the detent 33 of the latch member 27 when the latch member 27 is in the closed, inoperative position and thereby prevent actuation of the substance supply unit 20, and an engagement surface 59, here an outwardly and rearwardly flaring surface, which is such as to maintain the latch member 27 in the open position following commencement of operation of the substance supply unit 20.

In this embodiment the substance supply unit 20 is a single-dose unit for delivering a single metered dose of substance.

In another embodiment the substance supply unit 20 could be a duo-dose or multi-dose unit for delivering two or a plurality of metered doses of substance.

In this embodiment the substance supply unit 20 comprises a mechanical delivery pump, in particular a liquid delivery pump or a powder delivery pump, which delivers metered doses of a substance on actuation thereof.

In an alternative embodiment the substance supply unit 20 could comprise a dry powder delivery unit which delivers metered doses of a substance, as a dry powder, on actuation thereof.

In yet another alternative embodiment the substance supply unit 20 could comprise a nebulizer which delivers metered doses of a substance, as an aerosol spray, on actuation thereof.

In still another alternative embodiment the substance supply unit 20 could comprise an aerosol canister for delivering metered volumes of a propellant, preferably a hydrofluoroalkane (HFA) propellant or the like, containing substance, either as a suspension or solution.

FIGS. 4 to 7 illustrate a manually-actuated nasal delivery device in accordance with a second embodiment of the present invention.

The delivery device comprises a housing 115, a nosepiece 117 for fitting in a nasal cavity of a subject, a mouthpiece 119 into which the subject in use exhales, such as to enable delivery of an air flow into and through the nasal airway of the subject on exhalation by the subject through the mouthpiece 119, and a substance supply unit 120, which is manually actuatable to deliver substance to the nasal cavity of the subject.

The housing 115 comprises a body member 121, in this embodiment of substantially elongate, tubular section, which includes an aperture 123 at one end thereof, through which projects an actuating part of the substance supply unit 120, in this embodiment as defined by the base of a substance-containing chamber 151.

Figure 6:
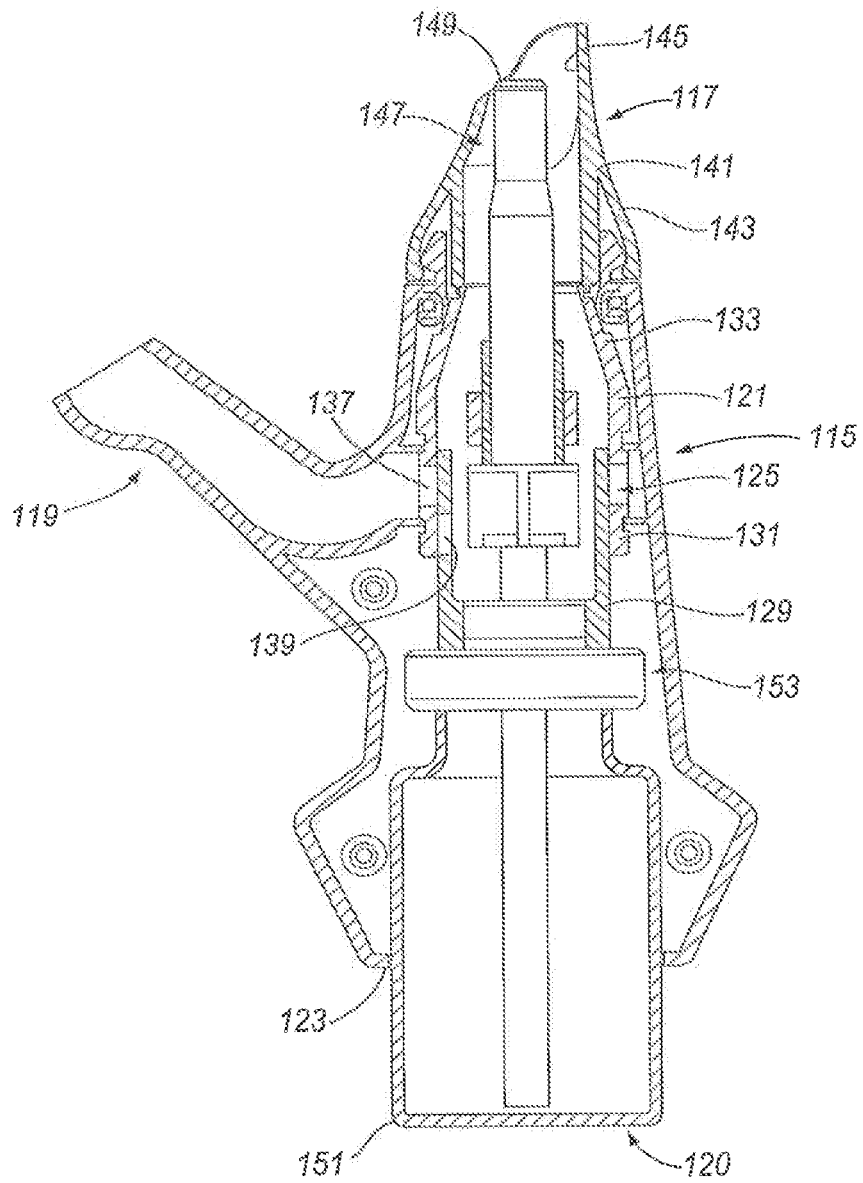
Figure 7:
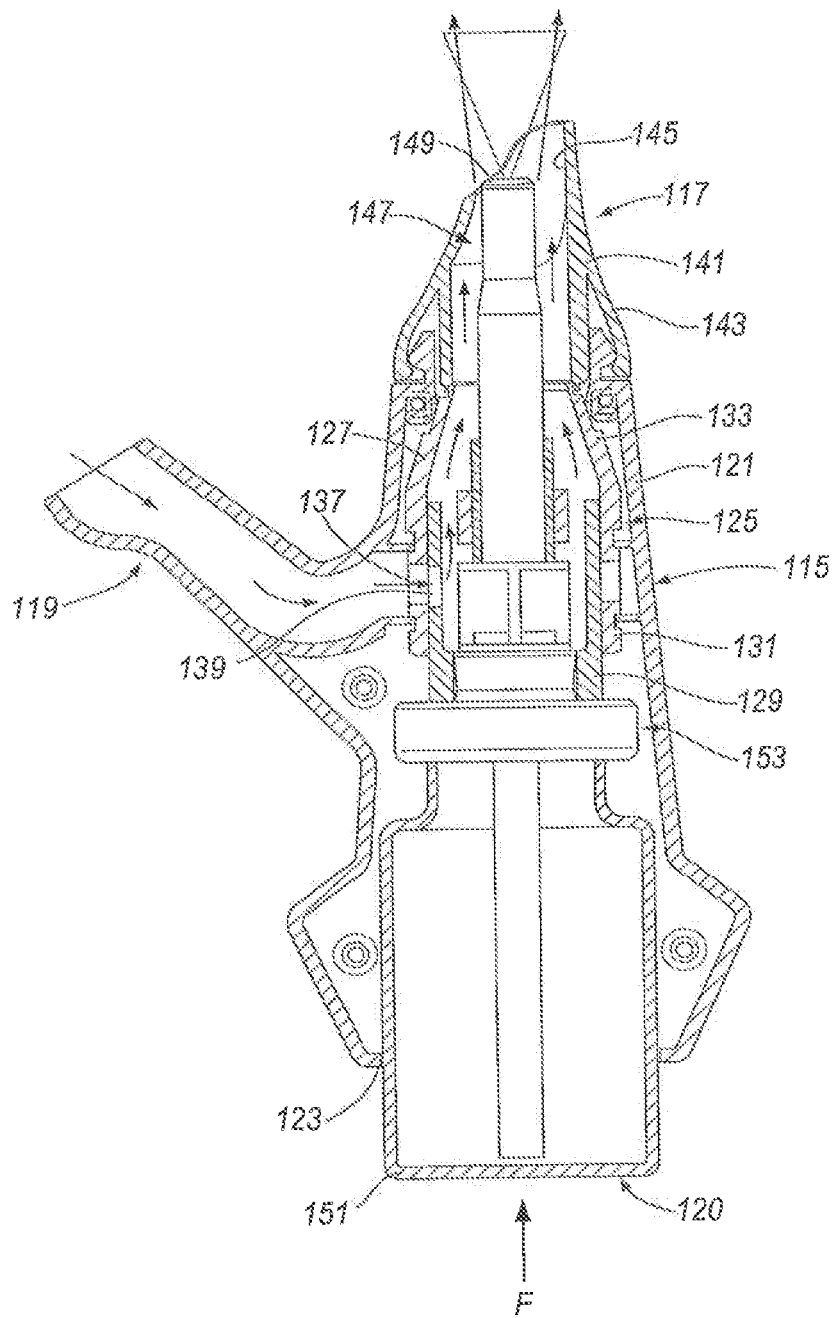
Figure 8:
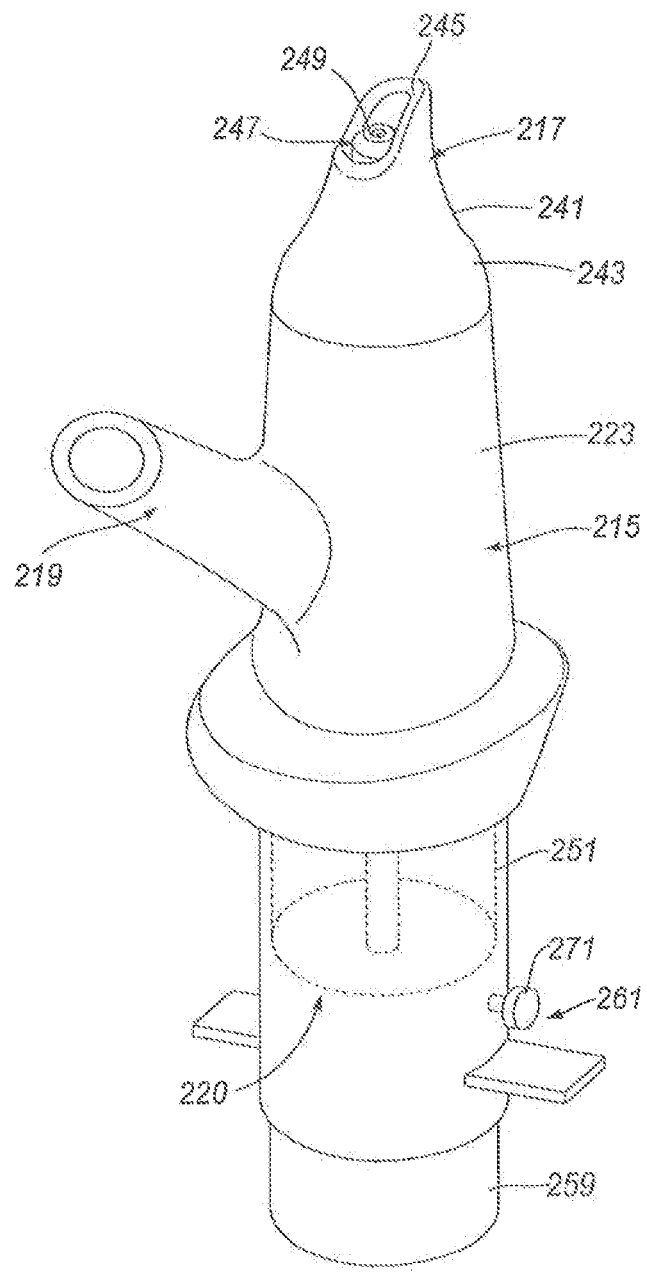
FIGS. 8 to 12 illustrate a nasal delivery device in accordance with a third embodiment of the present invention.
Figure 9:
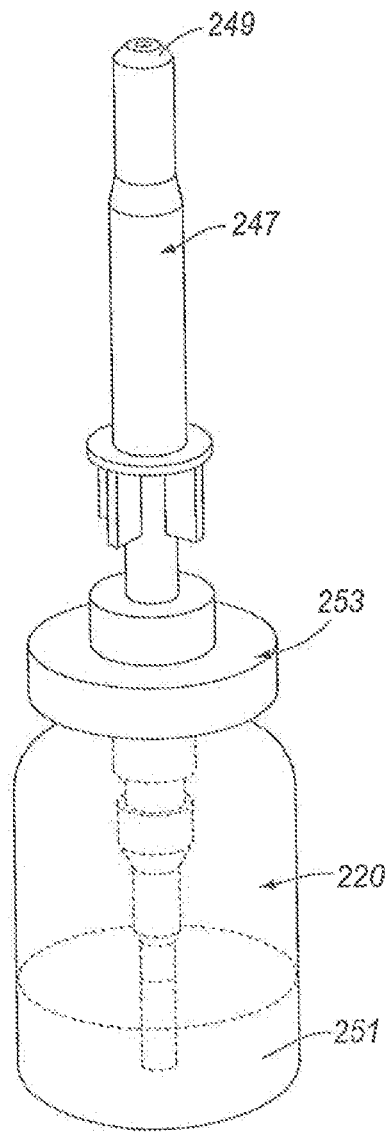

The housing 115 further comprises a valve assembly 125 which is fluidly connected to the nosepiece 117 and the mouthpiece 119, and operable between closed and open configurations, as illustrated in FIGS. 6 and 7, such as to provide for an air flow, in this embodiment in the form of a burst of air, through the nosepiece 117 simultaneously with actuation of the substance supply unit 120, as will be described in more detail hereinbelow.

The valve assembly 125 comprises a main, body element 127 and a valve element 129 which is slideably disposed to the body element 127 between closed and open positions, as illustrated in FIGS. 6 and 7.

The body element 127 comprises a valve section 131, in this embodiment a tubular section, in which the valve element 129 is slideably disposed, and an inwardly flaring forward section 133, in this embodiment having an inwardly tapering section, which is downstream of the valve section 131 and fluidly connected to the nosepiece 117.

The valve section 131 of the body element 127 and the valve element 129 each include a valve aperture 137, 139, which are fluidly isolated when the valve element 129 is in the closed position, as illustrated in FIG. 6, and in fluid communication when the valve element 129 is in the open position, as illustrated in FIG. 7.

The nosepiece 117 comprises a body member 141 which defines an outer sealing surface 143 for providing a sealing fit between the nosepiece 117 and a nasal cavity of the subject, and an inner delivery channel 145, which is in selective fluid communication with the mouthpiece 119 such that an air flow is selectively delivered into and through the nasal airway of the subject on exhalation by the subject through the mouthpiece 119, and an outlet unit 147 for delivering substance into the nasal airway of the subject, which is disposed within the delivery channel 145.

In this embodiment the outlet unit 147 comprises a nozzle 149 for delivering substance to the nasal airway of the subject. In this embodiment the nozzle 149 is disposed in the delivery channel 145 co-axially with the same. In this embodiment the nozzle 149 is configured to provide an aerosol spray. In an alternative embodiment, for the delivery of a liquid, the nozzle 149 could be configured to deliver a liquid jet as a column of liquid.

In a preferred embodiment the distal end of the outlet unit 147 is configured to extend at least about 2 cm, preferably at least about 3 cm, and more preferably from about 2 cm to about 3 cm, into the nasal cavity of the subject.

In this embodiment the substance supply unit 120 is a pump unit, which comprises a substance-containing chamber 151 which contains substance and extends from the aperture 123 in the housing 115 as the actuating part of the substance supply unit 120, and a mechanical delivery pump 153 which is actuatable, here by depression of the substance-containing chamber 151, typically by a finger or thumb of the subject, to deliver a metered dose of substance from the substance-containing chamber 151 to the outlet unit 147 and from the nozzle outlet 149 thereof, here as an aerosol spray.

In this embodiment the substance-containing chamber 151 is coupled to the valve element 129 of the valve assembly 125, such as to be moved therewith and simultaneously provide for actuation of the substance supply unit 120 and opening of the valve assembly 125, whereby substance, here in the form of a spray, and an air flow, here as a burst of air, are simultaneously delivered to the nasal cavity of the subject.

In this embodiment the mechanical delivery pump 153 is a liquid delivery pump for delivering a metered dose of substance, but in an alternative embodiment the mechanical delivery pump 153 could be a powder delivery pump, which delivers metered doses of a powdered substance on actuation thereof.

In this embodiment the substance supply unit 120 is a multi-dose unit for delivering a plurality of metered doses of substance in successive delivery operations.

In an alternative embodiment the substance supply unit 120 could be a single-dose unit for delivering a single metered dose of substance or a duo-dose unit for delivering two metered doses of substance in two successive delivery operations.

In another alternative embodiment the substance supply unit 120 could comprise a dry powder delivery unit which delivers metered doses of a substance, as a dry powder, on actuation thereof.

In yet another alternative embodiment the substance supply unit 120 could comprise a nebulizer which delivers metered doses of a substance, as an aerosol spray, on actuation thereof.

In still another alternative embodiment the substance supply unit 120 could comprise an aerosol canister for delivering metered volumes of a propellant, preferably a hydrofluoroalkane (HFA) propellant or the like, containing substance, either as a suspension or solution.

FIGS. 8 to 12 illustrate a manually-actuated nasal delivery device in accordance with a third embodiment of the present invention.

The delivery device comprises a housing 215, a nosepiece 217 for fitting in a nasal cavity of a subject, a mouthpiece 219 into which the subject in use exhales, such as to enable delivery of an air flow into and through the nasal airway of the subject on exhalation by the subject through the mouthpiece 219, a substance supply unit 220, which is actuatable to deliver substance to the nasal cavity of the subject, and a loading mechanism 221, which is operable to be primed with a loading force and manually actuatable to apply the loading force to the substance supply unit 220, such as to actuate the same.

Figure 10:
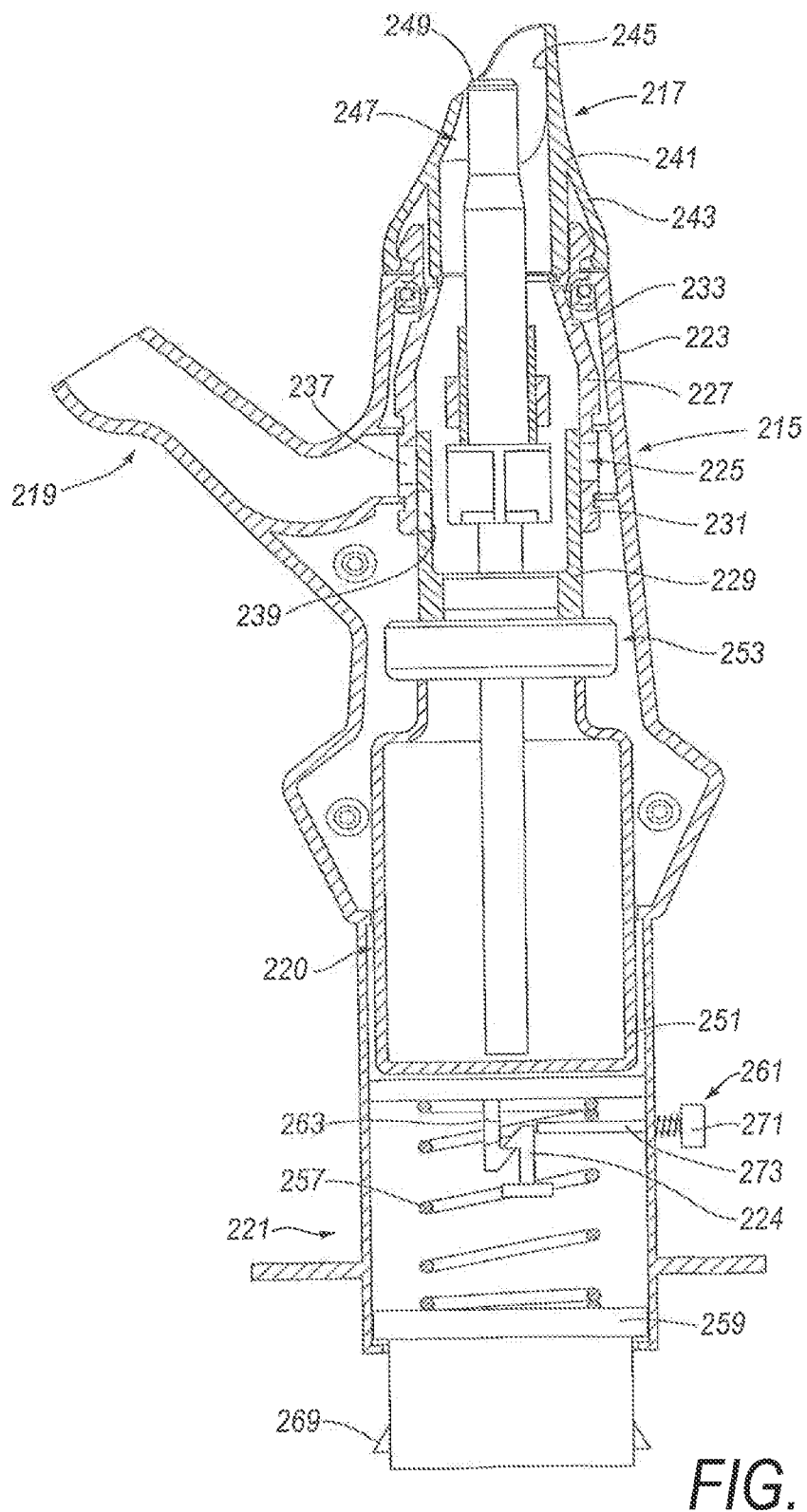
Figure 12:
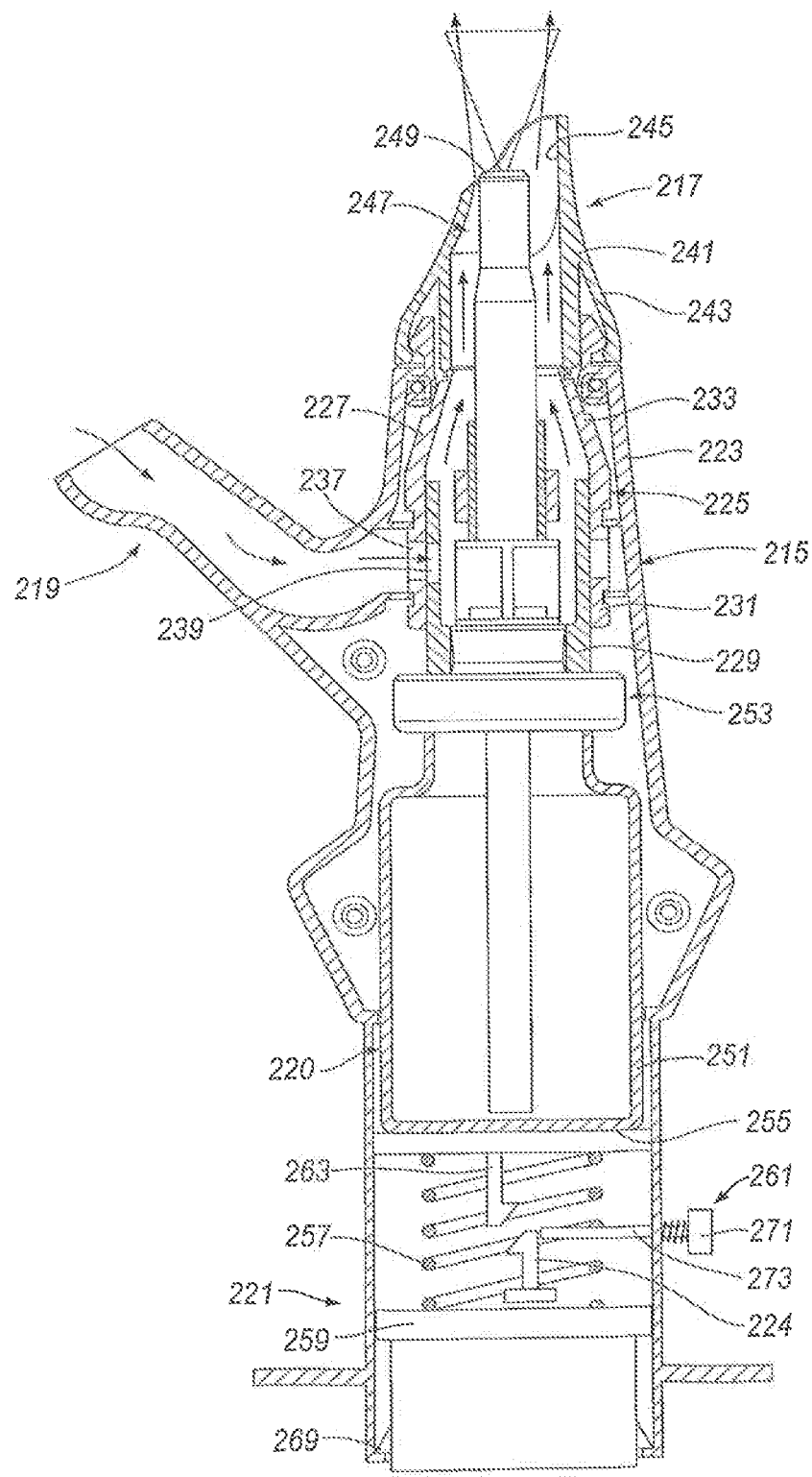

The housing 215 comprises a body member 223, in this embodiment of substantially elongate, tubular section, and a valve assembly 225 which is fluidly connected to the nosepiece 217 and the mouthpiece 219, and operable between closed and open configurations, as illustrated in FIGS. 10 and 12, such as to provide for an air flow, in this embodiment in the form of a burst of air, through the nosepiece 217 simultaneously with actuation of the substance supply unit 220, as will be described in more detail hereinbelow.

The body member 223 includes a latch element 224, in this embodiment a detent, for latching the loading member 259 of the loading mechanism 221 when in the primed position, as will be described in more detail hereinbelow.

The valve assembly 225 comprises a main, body element 227 and a valve element 229 which is slideably disposed to the body element 227 between closed and open positions, as illustrated in FIGS. 10 and 12.

The body element 227 comprises a valve section 231, in this embodiment a tubular section, in which the valve element 229 is slideably disposed, and an inwardly flaring forward section 233, in this embodiment having an inwardly tapering section, which is downstream of the valve section 231 and fluidly connected to the nosepiece 217.

The valve section 231 of the body element 227 and the valve element 229 each include a valve aperture 237, 239, which are fluidly isolated when the valve element 229 is in the closed position, as illustrated in FIG. 10, and in fluid communication when the valve element 229 is in the open position, as illustrated in FIG. 12.

The nosepiece 217 comprises a body member 241 which defines an outer sealing surface 243 for providing a sealing fit between the nosepiece 217 and a nasal cavity of the subject, and an inner delivery channel 245, which is in selective fluid communication with the mouthpiece 219, such that an air flow is selectively delivered into and through the nasal airway of the subject on exhalation by the subject through the mouthpiece 219, and an outlet unit 247 for delivering substance into the nasal airway of the subject, which is disposed within the delivery channel 245.

In this embodiment the outlet unit 247 comprises a nozzle 249 for delivering substance to the nasal airway of the subject. In this embodiment the nozzle 249 is disposed in the delivery channel 245 co-axially with the same. In this embodiment the nozzle 249 is configured to provide an aerosol spray. In an alternative embodiment, for the delivery of a liquid, the nozzle 249 could be configured to deliver a liquid jet as a column of liquid.

In a preferred embodiment the distal end of the outlet unit 247 is configured to extend at least about 2 cm, preferably at least about 3 cm, and more preferably from about 2 cm to about 3 cm, into the nasal cavity of the subject.

In this embodiment the substance supply unit 220 is a pump unit, which comprises a substance-containing chamber 251 which contains substance and is disposed within the body member 223 of the housing 215, and a mechanical delivery pump 253 which is actuatable to deliver a metered dose of substance from the substance-containing chamber 251 to the outlet unit 247 and from the nozzle outlet 249 thereof, here as an aerosol spray.

In this embodiment the substance-containing chamber 251 is coupled to the valve element 229 of the valve assembly 225, such as to be moved therewith and simultaneously provide for actuation of the substance supply unit 220 and opening of the valve assembly 225, whereby substance, here in the form of a spray, and an air flow, here as a burst of air, are simultaneously delivered to the nasal cavity of the subject.

In this embodiment the mechanical delivery pump 253 is a liquid delivery pump for delivering a metered dose of substance, but in an alternative embodiment the mechanical delivery pump 253 could be a powder delivery pump, which delivers metered doses of a powdered substance on actuation thereof.

In this embodiment the substance supply unit 220 is a multi-dose unit for delivering a plurality of metered doses of substance in successive delivery operations.

In an alternative embodiment the substance supply unit 220 could be a single-dose unit for delivering a single metered dose of substance or a duo-dose unit for delivering two metered doses of substance in two successive delivery operations.

In another alternative embodiment the substance supply unit 220 could comprise a dry powder delivery unit which delivers metered doses of a substance, as a dry powder, on actuation thereof.

In yet another alternative embodiment the substance supply unit 220 could comprise a nebulizer which delivers metered doses of a substance, as an aerosol spray, on actuation thereof.

In still another alternative embodiment the substance supply unit 220 could comprise an aerosol canister for delivering metered volumes of a propellant, preferably a hydrofluoroalkane (HFA) propellant or the like, containing substance, either as a suspension or solution.

The loading mechanism 221 comprises a drive member 255 which is loaded with a delivery force, a biasing element 257, in this embodiment a resilient element, here a compression spring, which, when loaded, applies the delivery force to the drive member 255, a loading member 259 which is manually operable to load the biasing element 257 to provide the delivery force, and an actuating member 261 which is manually actuatable to release the drive member 255 under the bias of the biasing element 257. The actuating member 261 can be located in any convenient position, and can, for example, be positioned to accommodate patient instructions. For example, in one embodiment the index finger can be utilized to fixate and retract the are of the inlet nostril over the nosepiece 217 to provide for improved delivery. In this embodiment the actuating member 261 could be positioned so as to actuatable by the thumb of the subject.

In this embodiment the drive member 255 includes a latch element 263, here a detent, which is a counterpart to the latch element 224 in the housing 215, and the latch elements 224, 263 are configured such as normally to latch the drive member 255 in a first, latched position, as illustrated in FIG. 10, and be released to a second, actuated position, as illustrated in FIG. 12, by manual actuation of the actuating member 261.

Figure 11:
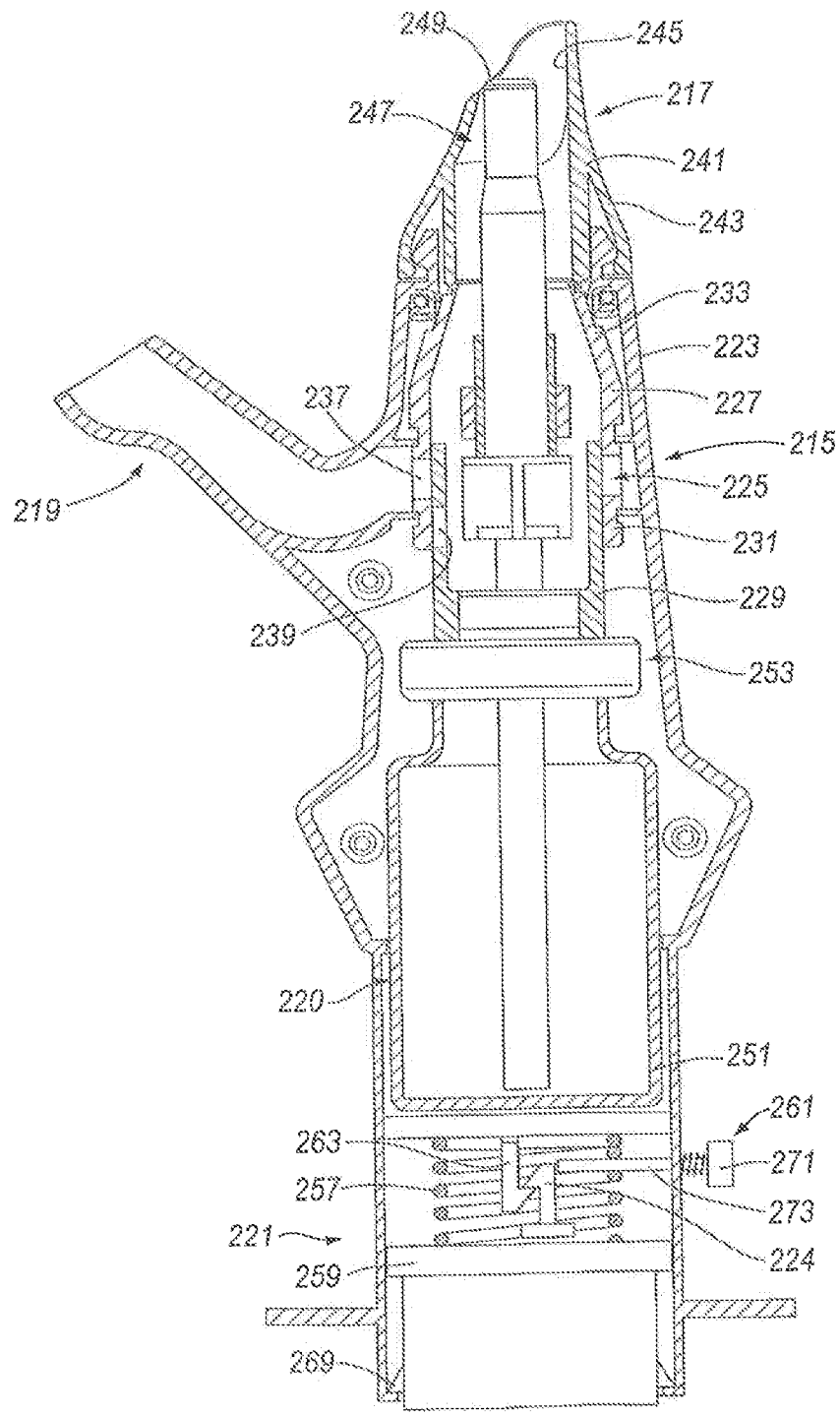

In this embodiment the loading member 259 includes a loading button 267 at one, the lower, end thereof, which is typically loaded by a finger or thumb of the user in loading the biasing element 257, and is moved from a first, unloaded position, as illustrated in FIG. 10 to a second, loaded position, as illustrated in FIG. 11.

In this embodiment the loading member 259 includes a detent 269, here an outwardly-directed flange, which acts to latch the loading member 259 in the loaded position, and thereby maintain the biasing element 257 in the loaded state against the drive member 255.

The actuating member 261 comprises an actuating button 271, which is manually operable by the subject, in this embodiment by a finger or thumb of the subject, and an operative element 273, in this embodiment a pin, which is coupled to the actuating button 271 and operable to displace the latching element 263 of the drive member 255 from latching engagement with the latching element 224 of the housing 215, such as to release the drive member 255 from the latched position, as illustrated in FIG. 11, to the actuated position, as illustrated in FIG. 12, in which the drive member 255 is driven to actuate the substance supply unit 220, in this embodiment by displacement of the substance-containing chamber 251, to deliver a dose of substance to the outlet unit 247 and from the nozzle 249 thereof, in this embodiment as an aerosol spray.

Figure 13:
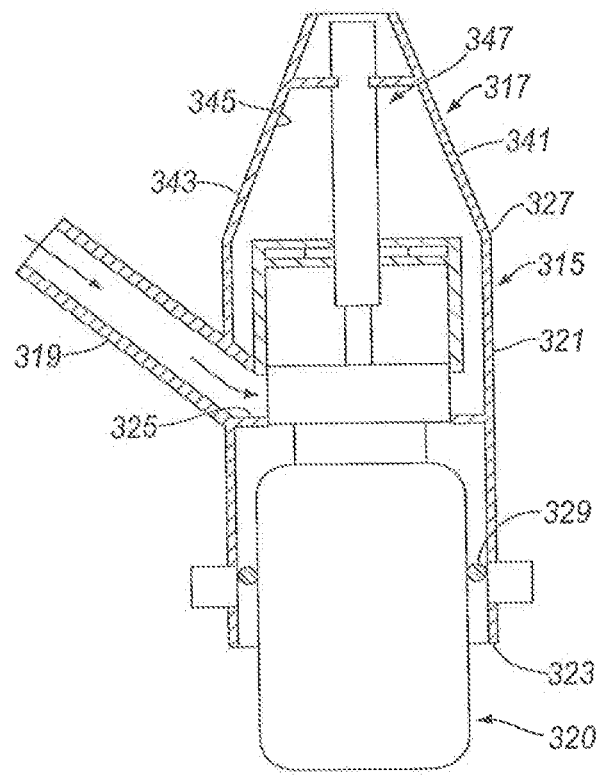
FIGS. 13 and 14 illustrate a nasal delivery device in accordance with a fourth embodiment of the present invention.
Figure 14:
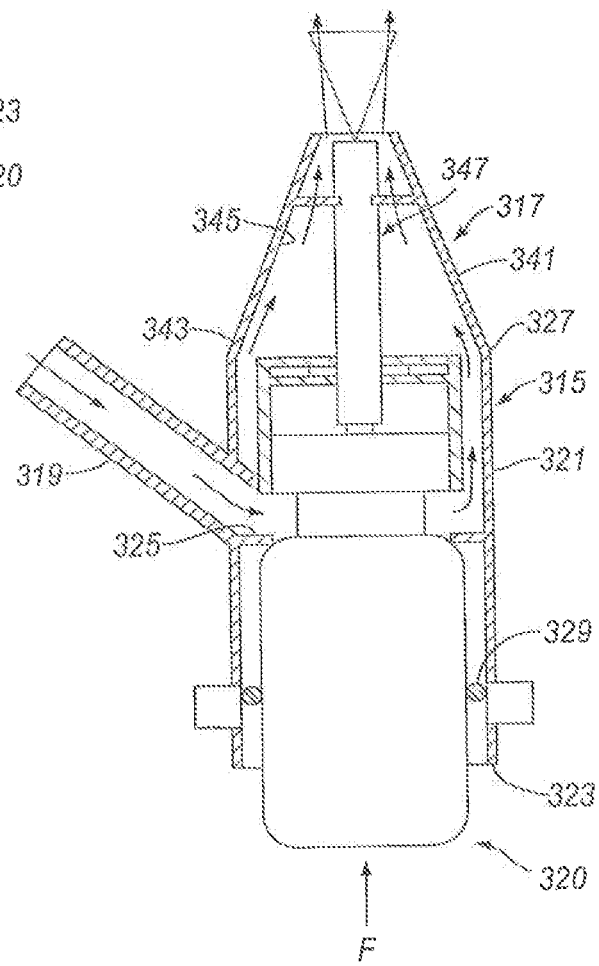

FIGS. 13 and 14 illustrate a manually-actuated nasal delivery device in accordance with a fourth embodiment of the present invention.

The delivery device comprises a housing 315, a nosepiece 317 for fitting in a nasal cavity of a subject, a mouthpiece 319 into which the subject in use exhales, such as to enable delivery of an air flow into and through the nasal airway of the subject on exhalation by the subject through the mouthpiece 319, and a substance supply unit 320, which is manually operable to deliver substance to the nasal cavity of the subject.

The housing 315 comprises a body member 321, in this embodiment of elongate, tubular section, which receives the substance supply unit 320 and includes an aperture 323 at one end thereof, through which projects an actuating part of the substance supply unit 320, in this embodiment as defined by a base of a substance-containing chamber 351.

The body member 321 further includes an inlet 325 which is in fluid communication with the mouthpiece 319, and an outlet 327 which is in fluid communication with the nosepiece 317.

The housing 315 further comprises a sealing element 329, in this embodiment an annular lip seal, which is disposed to the inner periphery of the body member 321 such as to provide for a sealing fit with the substance-containing chamber 351 and thereby preventing the escape of an exhalation air flow through the actuating aperture 323.

The nosepiece 317 comprises a body member 341 which defines an outer sealing surface 343 for providing a sealing fit between the nosepiece 317 and a nasal cavity of the subject, and an inner delivery channel 345, which is in selective fluid communication with the mouthpiece 319 such that an air flow is selectively delivered into and through the nasal airway of the subject on exhalation by the subject through the mouthpiece 319, and an outlet unit 347 for delivering substance into the nasal airway of the subject, which is disposed within the delivery channel 345.

In this embodiment the outlet unit 347 comprises a nozzle 349 for delivering substance to the nasal airway of the subject. In this embodiment the nozzle 349 is disposed in the delivery channel 345 co-axially with the same. In this embodiment the nozzle 349 is configured to provide an aerosol spray. In an alternative embodiment, for the delivery of a liquid, the nozzle 349 could be configured to deliver a liquid jet as a column of liquid.

In a preferred embodiment the distal end of the outlet unit 347 is configured to extend at least about 2 cm, preferably at least about 3 cm, and more preferably from about 2 cm to about 3 cm, into the nasal cavity of the subject.

In this embodiment the substance supply unit 320 is a pump unit, which comprises a substance-containing chamber 351 which contains substance and extends from the aperture 323 in the housing 315 as the actuating part of the substance supply unit 320, and a mechanical delivery pump 353 which is actuatable, here by depression of the substance-containing chamber 351 from an inoperative position, as illustrated in FIG. 13, to an actuated position, as illustrated in FIG. 14, such as to deliver a metered dose of substance from the substance-containing chamber 351 to the outlet unit 347 and from the nozzle outlet 349 thereof, here as an aerosol spray.

In this embodiment the substance-containing chamber 351 includes a body part 355, here a head part, which is configured such as to close the inlet 325 of the body member 321 when the substance supply unit 320 is in the inoperative or rest configuration, as illustrated in FIG. 13, such as to prevent the delivery of an air flow through the nosepiece 317 on exhalation by the subject into the mouthpiece 319, and open the inlet 325 of the body member 321 when the substance supply unit, 320 is in the actuated configuration, as illustrated in FIG. 14, such as to provide for an air flow, in this embodiment in the form of a burst of air, through the nosepiece 317 simultaneously with actuation of the substance supply unit 320.

In this embodiment the mechanical delivery pump 353 is a liquid delivery pump for delivering a metered dose of substance, but in an alternative embodiment the mechanical delivery pump 353 could be a powder delivery pump, which delivers metered doses of a powdered substance on actuation thereof.

In this embodiment the substance supply unit 320 is a multi-dose unit for delivering a plurality of metered doses of substance in successive delivery operations.

In an alternative embodiment the substance supply unit 320 could be a single-dose unit for delivering a single metered dose of substance or a duo-dose unit for delivering two metered doses of substance in two successive delivery operations.

In another alternative embodiment the substance supply unit 320 could comprise a dry powder delivery unit which delivers metered doses of a substance, as a dry powder, on actuation thereof.

In yet another alternative embodiment the substance supply unit 320 could comprise a nebulizer which delivers metered doses of a substance, as an aerosol spray, on actuation thereof.

In still another alternative embodiment the substance supply unit 320 could comprise an aerosol canister for delivering metered volumes of a propellant, preferably a hydrofluoroalkane (HFA) propellant or the like, containing substance, either as a suspension or solution.

Figure 15:
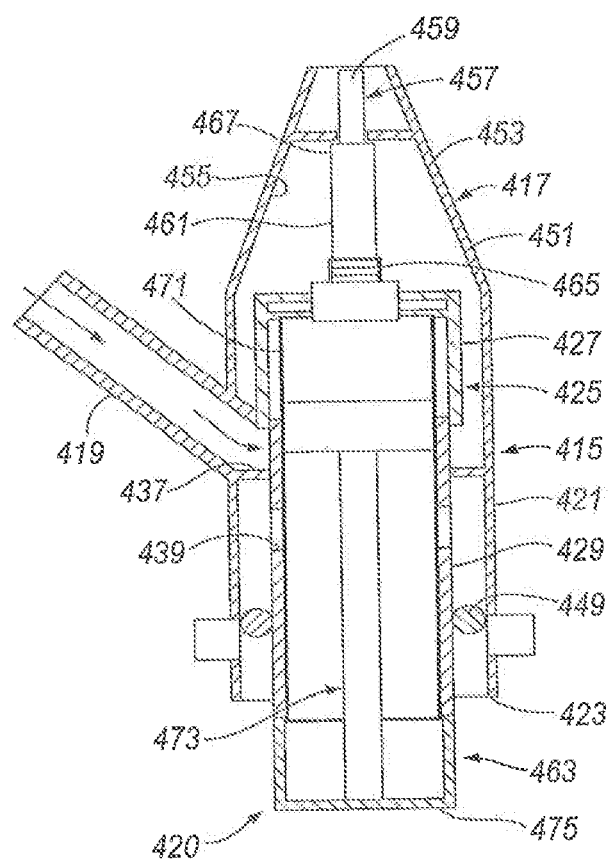
FIGS. 15 and 16 illustrate a nasal delivery device in accordance with a fifth embodiment of the present invention.
Figure 16:
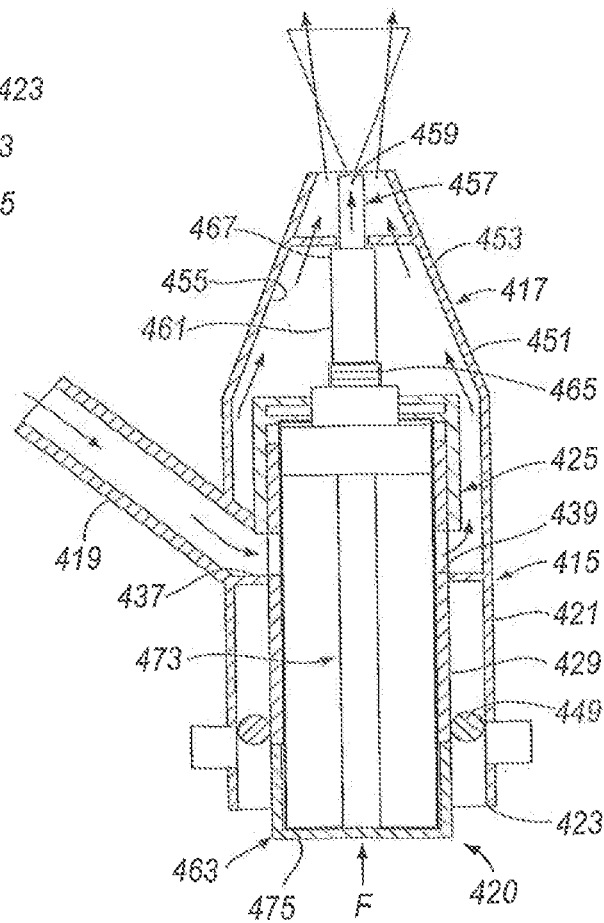
Figure 19:
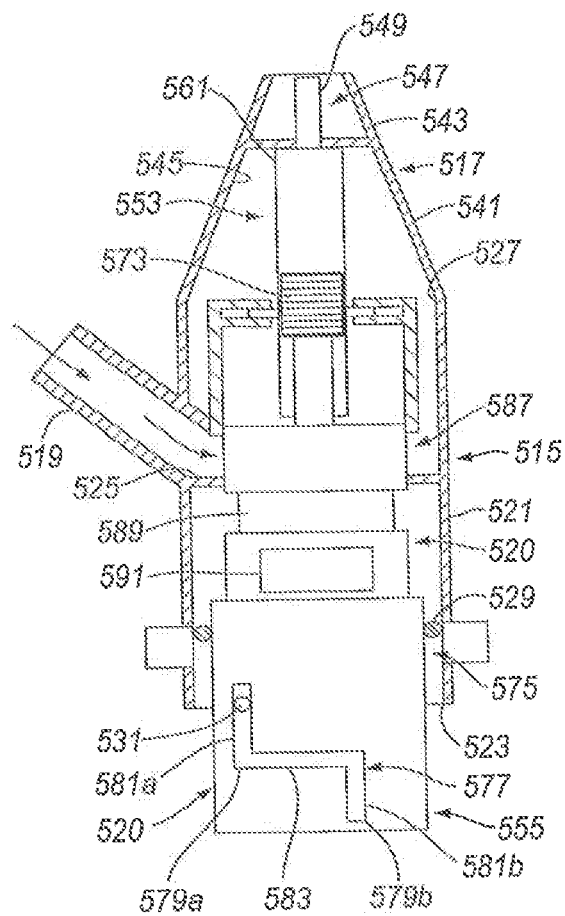

FIGS. 15 and 16 illustrate a manually-actuated nasal delivery device in accordance with a fifth embodiment of the present invention.

The delivery device comprises a housing 415, a nosepiece 417 for fitting in a nasal cavity of a subject, a mouthpiece 419 into which the subject in use exhales, such as to enable delivery of an air flow into and through the nasal airway of the subject on exhalation by the subject through the mouthpiece 419, and a substance supply unit 420, which is manually operable to deliver substance to the nasal cavity of the subject.

The housing 415 comprises a body member 421, in this embodiment of elongate, tubular section, which includes an aperture 423 at one end thereof, through which projects an actuating part of the substance supply unit 220, in this embodiment as defined by an actuating member 451.

The housing 415 further comprises a valve assembly 425 which is fluidly connected to the nosepiece 417 and the mouthpiece 419, and operable between closed and open configurations, as illustrated in FIGS. 15 and 16, such as to provide for an air flow, in this embodiment in the form of a burst of air, through the nosepiece 417 simultaneously with actuation of the substance supply unit 220, as will be described in more detail hereinbelow.

The valve assembly 425 comprises a main, body element 427, in this embodiment a tubular section, and a valve element 429, in this embodiment a tubular section, which is slideably disposed to the body element 427 between closed and open positions, as illustrated in FIGS. 15 and 16.

The body element 427 and the valve element 429 each include a valve aperture 437, 439, which are fluidly isolated when the valve element 429 is in the closed position, as illustrated in FIG. 15, and in fluid communication when the valve element 429 is in the open position, as illustrated in FIG. 16.

The housing 415 further comprises a sealing element 449, in this embodiment an annular lip seal, which is disposed to the inner periphery of the body member 421 such as to provide for a sealing fit with the valve element 429 of the valve assembly 425 and thereby prevent the escape of an exhalation air flow through the actuating aperture 423.

The nosepiece 417 comprises a body member 451 which defines an outer sealing surface 453 for providing a sealing fit between the nosepiece 417 and a nasal cavity of the subject, and an inner delivery channel 455, which is in selective fluid communication with the mouthpiece 419 such that an air flow is selectively delivered into and through the nasal airway of the subject on exhalation by the subject through the mouthpiece 419, and an outlet unit 457 for delivering substance into the nasal airway of the subject, which is disposed within the delivery channel 455.

In this embodiment the outlet unit 457 comprises a nozzle 459 for delivering substance to the nasal airway of the subject. In this embodiment the nozzle 459 is disposed in the delivery channel 455 co-axially with the same. In this embodiment the nozzle 459 is configured to provide an aerosol spray. In an alternative embodiment, the nozzle 459 could be configured to deliver a jet, as a column of powder, or a plume of powder.

In a preferred embodiment the distal end of the outlet unit 457 is configured to extend at least about 2 cm, preferably at least about 3 cm, and more preferably from about 2 cm to about 3 cm, into the nasal cavity of the subject.

In this embodiment the substance supply unit 420 is a pump unit, which comprises a substance-containing chamber 461 which contains a metered dose of substance and is fluidly connected to the outlet unit 457, and a mechanical delivery pump 463 which is actuatable to deliver an air flow through the substance-containing chamber 461, such as to entrain the substance from the substance-containing chamber 461 to the outlet unit 457 and from the nozzle outlet 459 thereof, here as an aerosol spray.

In this embodiment the substance-containing chamber 461 is a tubular section, typically of aluminium, polyethylene terepthalate (PET) or polycarbonate (PC), which includes an inlet which is fluidly connected to the mechanical delivery pump 463 and an outlet which is fluidly connected to the outlet unit 457, with the inlet and the outlet including frangible elements 465, 467, typically a foil, such as an aluminium-plastic laminate foil, heat sealed to the inlet and outlet, which normally contain the substance in the substance-containing chamber 461 and are ruptured on actuation of the mechanical delivery pump 463.

In this embodiment the mechanical delivery pump 463 comprises an air chamber 471 which is fluidly connected to the inlet of the sub stance-containing chamber 461 and a piston member 473 which is movably disposed in the air chamber 471 between a rest configuration, as illustrated in FIG. 15, and an actuated position, as illustrated in FIG. 16, in which the piston member 473 is driven into the air chamber 471, such as to compress and expel the air as contained thereby.

In this embodiment the piston member 473 includes an actuator element 475, here in the form of a button, which extends from the actuating aperture 423 in the housing 415 and is operable by a finger or thumb of the subject.

In this embodiment the piston member 473 is coupled to the valve element 429 of the valve assembly 425, such as to be moved therewith. With this configuration, the valve element 429 is in the closed position when the piston member 473 is in the inoperative or rest position, as illustrated in FIG. 15, such as to prevent the delivery of an air flow through the nosepiece 417 on exhalation by the subject, and moved to the open position when the piston member is 473 is actuated, as illustrated in FIG. 16, such as to provide for an air flow, in this embodiment in the form of a burst of air, through the nosepiece 417 simultaneously with actuation of the substance supply unit 420.

In this embodiment the substance supply unit 420 is a single-dose unit for delivering a single metered dose of substance in a delivery operation. In one embodiment the substance-containing chamber 461 is replaceable, so as to allow re-use of the delivery device.

In one embodiment the piston member 473 can include a piercing element at the forward end thereof which acts to pierce one or both of the frangible elements 465, 467 on depression of piston member 473.

In one embodiment the substance-containing chamber 461 could be provided by a small-diameter tube, typically of a diameter of less than about 3 mm, and preferably between about 2 mm and 3 mm.

In another embodiment the substance-containing chamber 461 could be a capsule, such as a gelatin or hydroxypropylmethyl cellulose (HPMC) capsule. The capsule could be any of sizes 000, 00, 0, 1, 2, 3, 4 or 5.

In one embodiment the substance supply unit 420 could comprise a plurality of substance-containing chambers 461, typically from 2 to 6 substance-containing chambers 461, which are provided in a magazine, which is movable to present a successive one of the substance-containing chambers 461 for each actuation of the substance supply unit 420. In one embodiment the magazine could be a rotatable magazine. In another embodiment the magazine could be a flexible or rigid arrangement which is drawn laterally to put the respective substance-containing chamber 461 in communication with the mechanical delivery pump 463 and the outlet unit 457. In one embodiment the magazine could be replaceable, either as a separate component or as an integral component with the nosepiece 417.

In one embodiment the delivery device can include a rupturing element which is operative to provide for rupturing of the outlet of the substance-containing chamber 461 on replacement thereof. In one embodiment the rupturing element can be operatively coupled to the nosepiece 417, such as to provide for rupturing of the outlet of the substance-containing chamber 461 on fitting the nosepiece 417. In another embodiment, where the substance-containing chamber 461 is provided in a magazine, the rupturing element can be operatively coupled to the magazine, such as to provide for rupturing of the outlet of the substance-containing chamber 461 on movement of the magazine.

In one embodiment the delivery pump 463 can include a valve arrangement which provides that air is drawn from other than via the nosepiece 417 or mouthpiece 419, which may be contaminated, for example, by previously-delivered substance. In one embodiment the piston member 473 can include a flow channel which extends from the front, piston surface to the actuator element 475, such that, when the piston member 473 is withdrawn from the air chamber 471, air is drawn only via the flow channel, and, when the actuator element 475 is depressed by a finger or thumb of the subject, the finger or thumb closes the flow channel, which provides for compression of the air contained in the air chamber 471.

FIGS. 17 to 22 illustrate a manually-actuated nasal delivery device in accordance with a sixth embodiment of the present invention.

The delivery device comprises a housing 515, a nosepiece 517 for fitting in a nasal cavity of a subject, a mouthpiece 519 into which the subject in use exhales, such as to enable delivery of an air flow into and through the nasal airway of the subject on exhalation by the subject through the mouthpiece 519, and a substance supply unit 520, which is manually operable to deliver substance to the nasal cavity of the subject.

The housing 515 comprises a body member 521, in this embodiment of elongate, tubular section, which receives the substance supply unit 520 and includes an aperture 523 at one end thereof, through which projects an actuating part of the substance supply unit 520, in this embodiment as defined by an actuator member 555.

The body member 521 further includes an inlet 525 which is in fluid communication with the mouthpiece 519, and an outlet 527 which is in fluid communication with the nosepiece 517.

The housing 515 further comprises a sealing element 529, in this embodiment an annular lip seal, which is disposed to the inner periphery of the body member 521 such as to provide for a sealing fit with the actuator member 555 and thereby prevent the escape of an exhalation air flow through the actuating aperture 523.

The housing 515 further comprises a locator element 531, in this embodiment an inwardly-projecting lug, which is captively located in a track 577 in the actuator member 555, as will be described in more detail hereinbelow.

The nosepiece 517 comprises a body member 541 which defines an outer sealing surface 543 for providing a sealing fit between the nosepiece 517 and a nasal cavity of the subject, and an inner delivery channel 545, which is in selective fluid communication with the mouthpiece 519 such that an air flow is selectively delivered into and through the nasal airway of the subject on exhalation by the subject through the mouthpiece 519, and an outlet unit 547 for delivering substance into the nasal airway of the subject, which is disposed within the delivery channel 545.

In this embodiment the outlet unit 547 comprises a nozzle 549 for delivering substance to the nasal airway of the subject. In this embodiment the nozzle 549 is disposed in the delivery channel 545 co-axially with the same. In this embodiment the nozzle 549 is configured to provide an aerosol spray. In an alternative embodiment, for the delivery of a liquid, the nozzle 549 could be configured to deliver a liquid jet as a column of liquid.

In a preferred embodiment the distal end of the outlet unit 547 is configured to extend at least about 2 cm, preferably at least about 3 cm, and more preferably from about 2 cm to about 3 cm, into the nasal cavity of the subject.

In this embodiment the substance supply unit 520 is a pump unit, which comprises a mechanical delivery pump 553 which is operable to deliver a metered dose of substance to the outlet unit 547, and an actuator member 555 which is operable, here by depression thereof with a finger or thumb of the subject, to actuate the pump 553.

In this embodiment the pump 553 comprises a substance-containing chamber 561 which contains a volume of substance and is fluidly connected to the outlet unit 547, and a piston member 573 which is movable into the substance-containing chamber 561 between a plurality of respective positions, such as to deliver a metered dose of substance with each advance of the piston member 573 between respective ones of the positions. In this embodiment the pump 553 is a duo-dose pump which contains two metered doses of substance, and, in operation, the piston member 573 is advanced to two positions in successive delivery operations, as will be described in more detail hereinbelow.

The actuator member 555 comprises a body section 575, in this embodiment of cylindrical form, which is slideably disposed in the body member 521 of the housing 515, in this embodiment in sealing engagement with the sealing element 529 at the inner periphery of the body member 521, such as to prevent the escape of an air flow through the actuating aperture 523.

The body section 575 includes a track 577 in the outer, peripheral surface thereof, which receives the locator element 531 on the housing 515.

The track 577 defines a plurality of, in this embodiment two longitudinally-spaced stops 579a, 579b, which define respective positions of the actuator member 555 relative to the body member 521.

In this embodiment the track 577 includes first and second track sections 581a, 581b which extend in the longitudinal direction of the actuator member 555, with the respective outer ends of the track sections 581a, 581b defining the stops 579a, 579b, and a third track section 583, which interconnects the first and second track sections 581a, 581b and extends circumferentially. In this embodiment the locator element 531 is moved between the first and second track sections 581a, 581b by rotation of the actuator member 555 in the housing 515.

Figure 20:
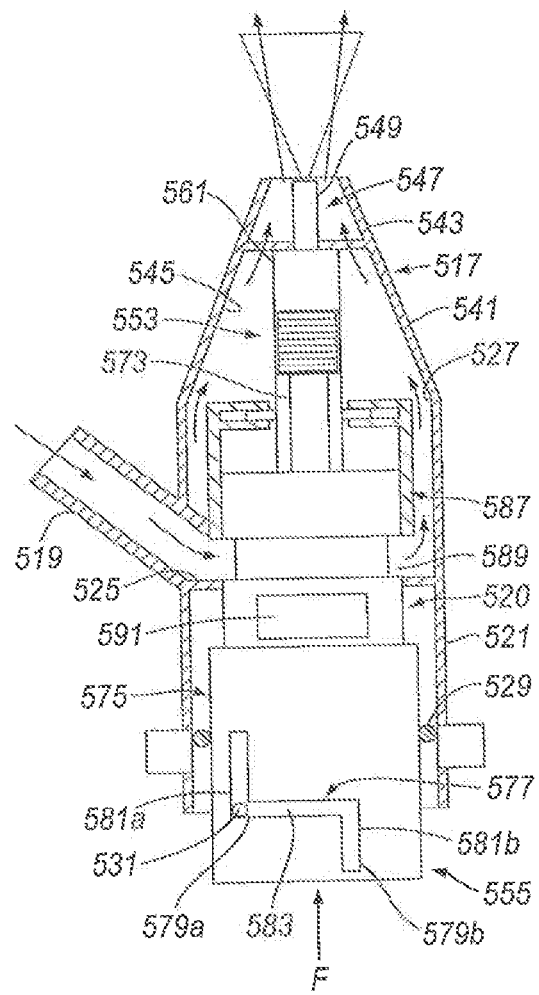
Figure 21:
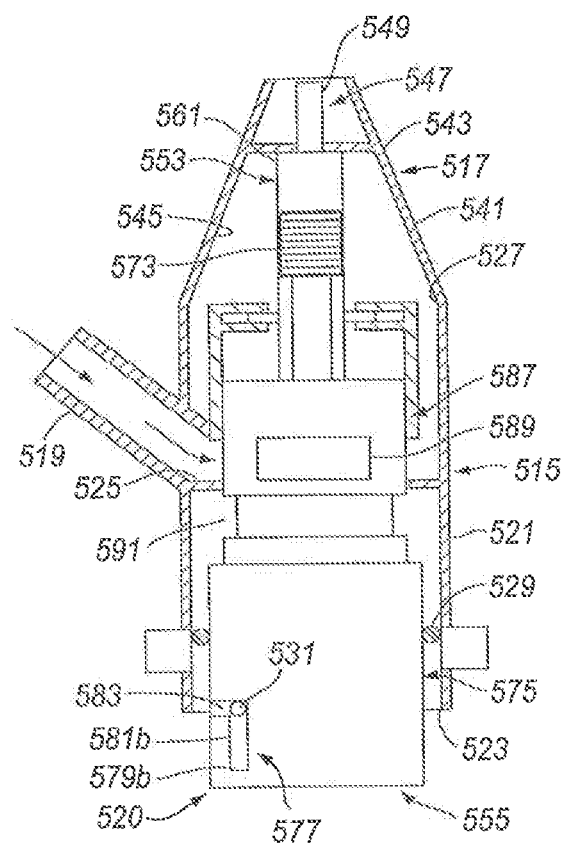
Figure 22:
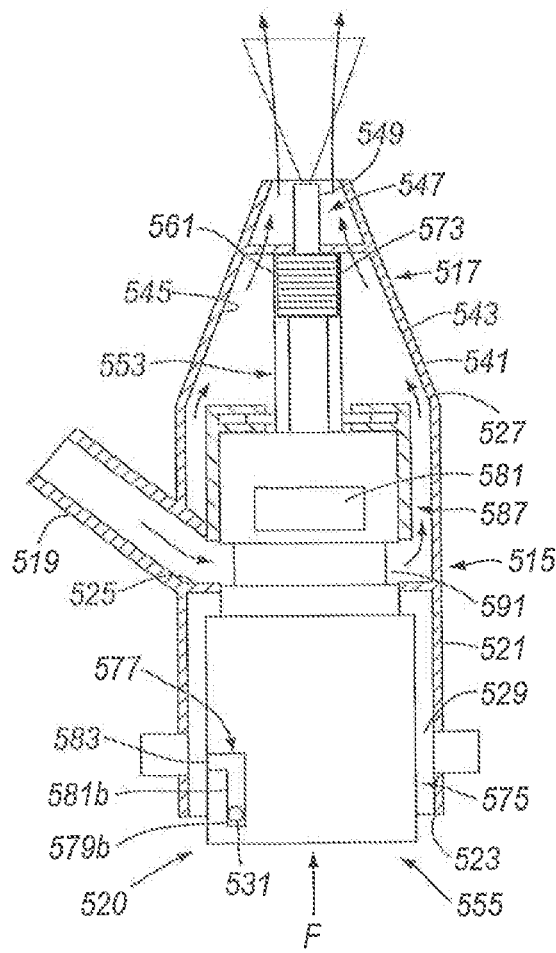

The actuator member 555 further comprises a valve section 587 which includes a plurality of, in this embodiment first and second valve apertures 589, 591, at longitudinally spaced locations, such that the first valve aperture 589 is in fluid communication with the inlet 525 of the housing 515 when the actuator member 555 is in a first actuated position, as illustrated in FIG. 20, and the second valve aperture 591 is in fluid communication with the inlet 525 of the housing 515 when the actuator member 555 is in a second actuated position, as illustrated in FIG. 22.

With this configuration, an air flow, in this embodiment in the form of a burst of air, is delivered through the nosepiece 517 simultaneously with actuation of the substance supply unit 520 in delivering a dose of substance to the nasal cavity of the subject.

In this embodiment the pump 553 is a liquid delivery pump for delivering a metered dose of substance, but in an alternative embodiment the pump 553 could be a powder delivery pump, which delivers metered doses of a powdered substance on actuation thereof.

In another alternative embodiment the substance supply unit 520 could comprise a dry powder delivery unit which delivers metered doses of a substance, as a dry powder, on actuation thereof.

In yet another alternative embodiment the substance supply unit 520 could comprise a nebulizer which delivers metered doses of a substance, as an aerosol spray, on actuation thereof.

In still another alternative embodiment the substance supply unit 520 could comprise an aerosol canister for delivering metered volumes of a propellant, preferably a hydrofluoroalkane (HFA) propellant or the like, containing substance, either as a suspension or solution.

FIGS. 23 and 24 illustrate a manually-actuated nasal delivery device in accordance with a seventh embodiment of the present invention.

The delivery device comprises a housing 615, a nosepiece 617 for fitting in a nasal cavity of a subject, a mouthpiece 619 into which the subject in use exhales, such as to enable delivery of an air flow into and through the nasal airway of the subject on exhalation by the subject through the mouthpiece 619, and a substance supply unit 620, which is manually operable to deliver substance to the nasal cavity of the subject.

The housing 615 comprises a body member 621, in this embodiment of elongate, tubular section, which receives the substance supply unit 620 and includes an aperture 623 at one end thereof, through which projects an actuating part of the substance supply unit 620, in this embodiment as defined by a base of a substance-containing chamber 651.

The body member 621 further includes an inlet 625 which is in fluid communication with the mouthpiece 619, and an outlet 627 which is in fluid communication with the nosepiece 617.

The body member 621 includes a flow regulator 629 which functions, with actuating movement of the substance supply unit 620, to regulate the flow characteristics, including flow rate, flow profile and flow duration, of an exhalation air flow as delivered between the inlet 625 and outlet 627 of the body member 621. The present inventors have determined that, by regulating the flow characteristics of the exhalation air flow, the deposition pattern of the delivered substance can be significantly altered, thereby providing a simple mechanism for controlling the deposition characteristics of the delivered substance.

In this embodiment the flow regulator 629, here in the form of an annular element, includes an aperture 631 into which extends a movable part of the substance supply unit 620, such that, with actuating movement of the substance supply unit 620, the effective area of the flow channel between the inlet 625 and the outlet 627 has a predetermined profile over the duration of the actuating movement of the substance supply unit 620.

In this embodiment the flow regulator 629 provides substantially for closure of the flow channel between the inlet 625 and the outlet 627 at the end of the end of the actuating movement (stroke) of the substance supply unit 620.

In an alternative embodiment the flow regulator 629 could provide for partial closure of the flow channel between the inlet 625 and the outlet 627 at the end of the end of the actuating movement (stroke) of the substance supply unit 620, for example, a 50% reduction in the effective area of the flow channel.

In this embodiment the housing 615 includes a tubular section 635 which provides for a sealing fit with the substance-containing chamber 651 and thereby prevents the escape of an exhalation air flow through the actuating aperture 623.

FIG. 25 illustrates flow profiles achieved in devices having (I) a flow regulator 629 which substantially closes the flow channel at the end of actuating movement of the substance supply unit 620, (II) a flow regulator 629 which provides for a 50% reduction in the effective area of the flow channel at the end of actuating movement of the substance supply unit 620, and (III) no flow regulation, for exhalation air flows of a 2 second duration.

The nosepiece 617 comprises a body member 641 which defines an outer sealing surface 643 for providing a sealing fit between the nosepiece 617 and a nasal cavity of the subject, and an inner delivery channel 645, which is in selective fluid communication with the mouthpiece 619 such that an air flow is selectively delivered into and through the nasal airway of the subject on exhalation by the subject through the mouthpiece 619, and an outlet unit 647 for delivering substance into the nasal airway of the subject, which is disposed within the delivery channel 645.

In this embodiment the outlet unit 647 comprises a nozzle 649 for delivering substance to the nasal airway of the subject. In this embodiment the nozzle 649 is disposed in the delivery channel 645 co-axially with the same. In this embodiment the nozzle 649 is configured to provide an aerosol spray. In an alternative embodiment, for the delivery of a liquid, the nozzle 649 could be configured to deliver a liquid jet as a column of liquid.

In a preferred embodiment the distal end of the outlet unit 647 is configured to extend at least about 2 cm, preferably at least about 3 cm, and more preferably from about 2 cm to about 3 cm, into the nasal cavity of the subject.

Figure 23:
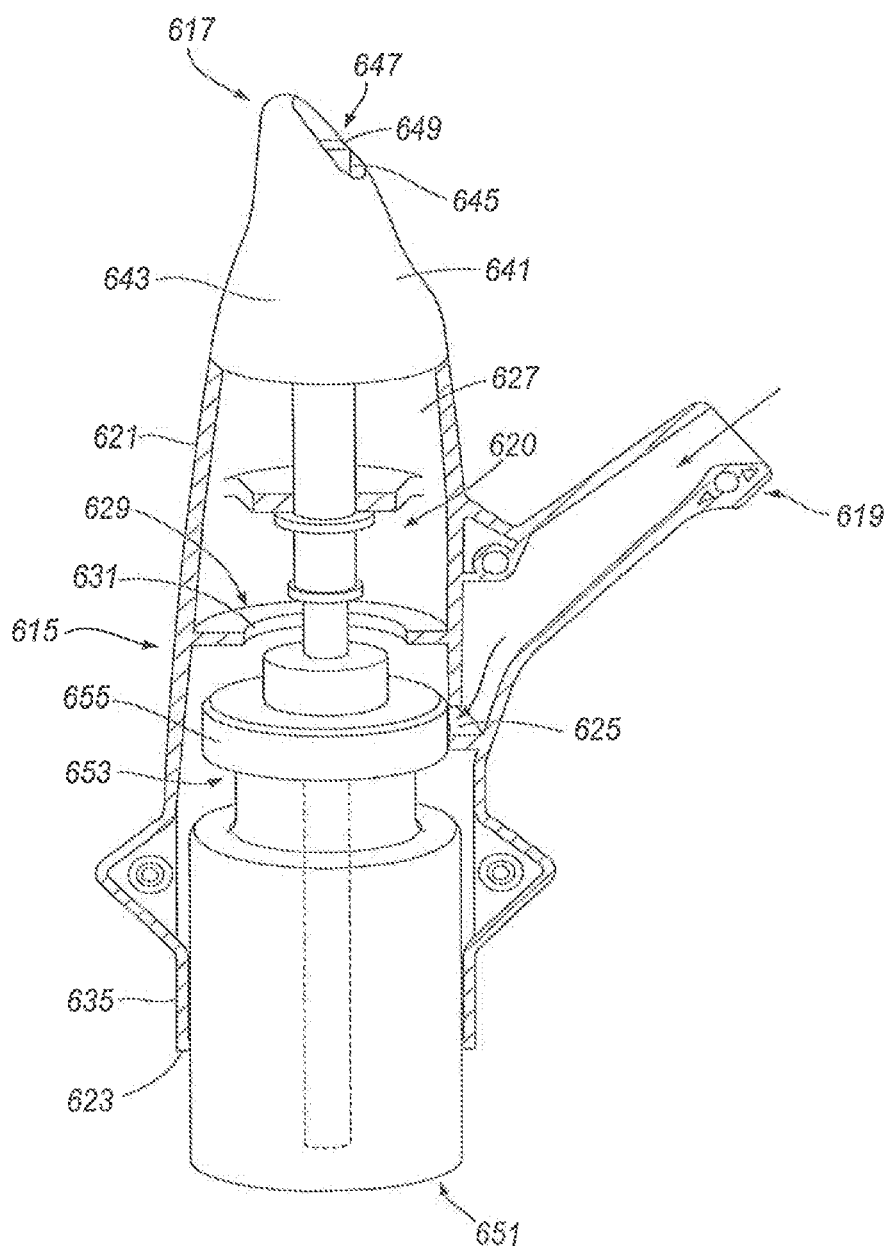
FIGS. 23 and 24 illustrate a nasal delivery device in accordance with a seventh embodiment of the present invention.
Figure 24:
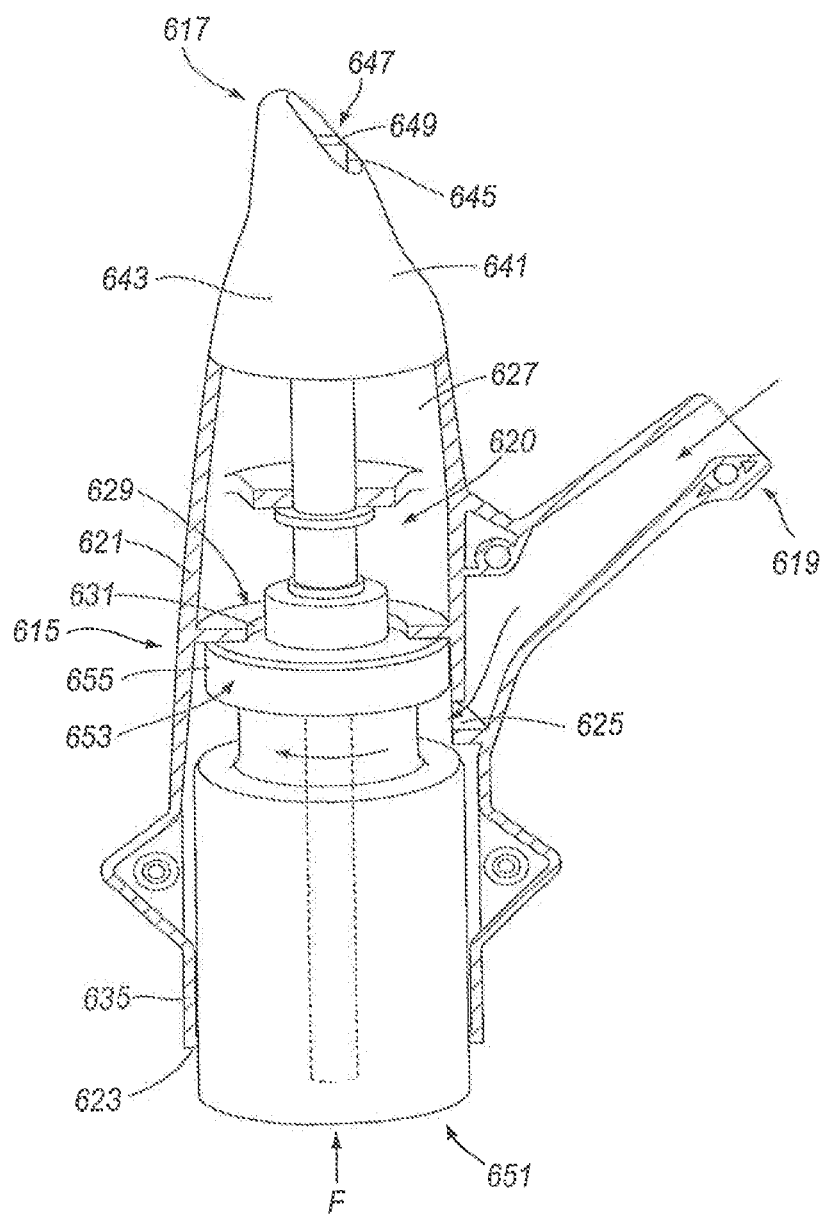
Figure 25:
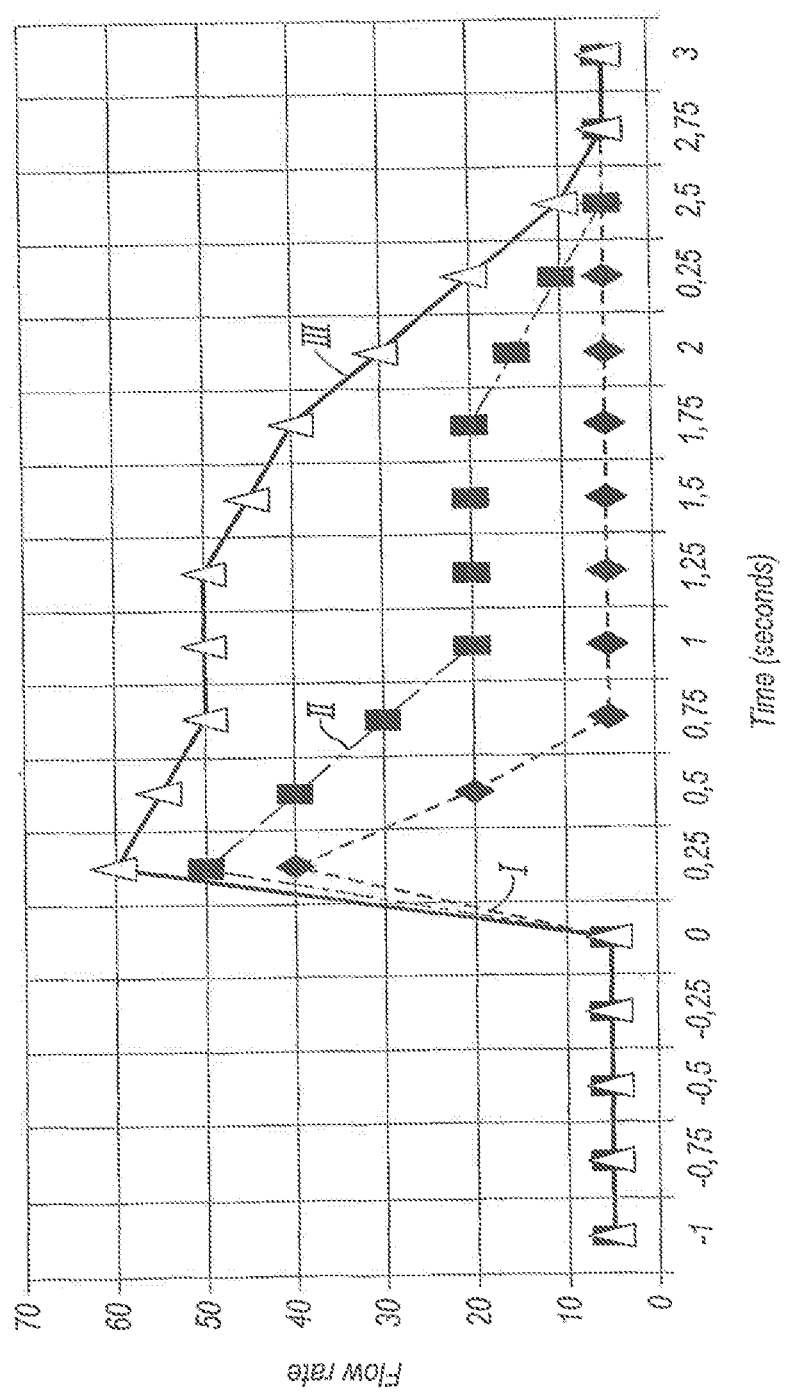
FIG. 25 illustrates flow profiles for the delivery device of FIG. 7.

In this embodiment the substance supply unit 620 is a pump unit, which comprises a substance-containing chamber 651 which contains substance and extends from the aperture 623 in the housing 615 as the actuating part of the substance supply unit 620, and a mechanical delivery pump 653 which is actuatable, here by depression of the substance-containing chamber 651 from an inoperative position, as illustrated in FIG. 23, to an actuated position, as illustrated in FIG. 24, such as to deliver a metered dose of substance from the substance-containing chamber 651 to the outlet unit 647 and from the nozzle outlet 649 thereof, here as an aerosol spray.

In this embodiment the substance-containing chamber 651 includes a body part 655, here a head part, which is configured such as to close the inlet 625 of the body member 621 when the substance supply unit 620 is in the inoperative or rest configuration, as illustrated in FIG. 23, such as substantially to prevent the delivery of an air flow through the nosepiece 617 on exhalation by the subject into the mouthpiece 619, and open the inlet 625 of the body member 621 when the substance supply unit 620 is in the actuated configuration, as illustrated in FIG. 24, such as to provide for an air flow, in this embodiment in the form of a burst of air, through the nosepiece 617 simultaneously with actuation of the substance supply unit 620. As described above, the body part 655 also functions with the flow regulator 629 to alter the flow characteristics of the exhaled air flow, in this embodiment substantially to close the flow channel on movement of the substance supply unit 620 to the actuated configuration.

In this embodiment the mechanical delivery pump 653 is a liquid delivery pump for delivering a metered dose of substance, but in an alternative embodiment the mechanical delivery pump 653 could be a powder delivery pump, which delivers metered doses of a powdered substance on actuation thereof.

In this embodiment the substance supply unit 620 is a multi-dose unit for delivering a plurality of metered doses of substance in successive delivery operations.

In an alternative embodiment the substance supply unit 620 could be a single-dose unit for delivering a single metered dose of substance or a duo-dose unit for delivering two metered doses of substance in two successive delivery operations.

In another alternative embodiment the substance supply unit 620 could comprise a dry powder delivery unit which delivers metered doses of a substance, as a dry powder, on actuation thereof.

In yet another alternative embodiment the substance supply unit 620 could comprise a nebulizer which delivers metered doses of a substance, as an aerosol spray, on actuation thereof.

In still another alternative embodiment the substance supply unit 620 could comprise an aerosol canister for delivering metered volumes of a propellant, preferably a hydrofluoroalkane (HFA) propellant or the like, containing substance, either as a suspension or solution.

Figure 26:
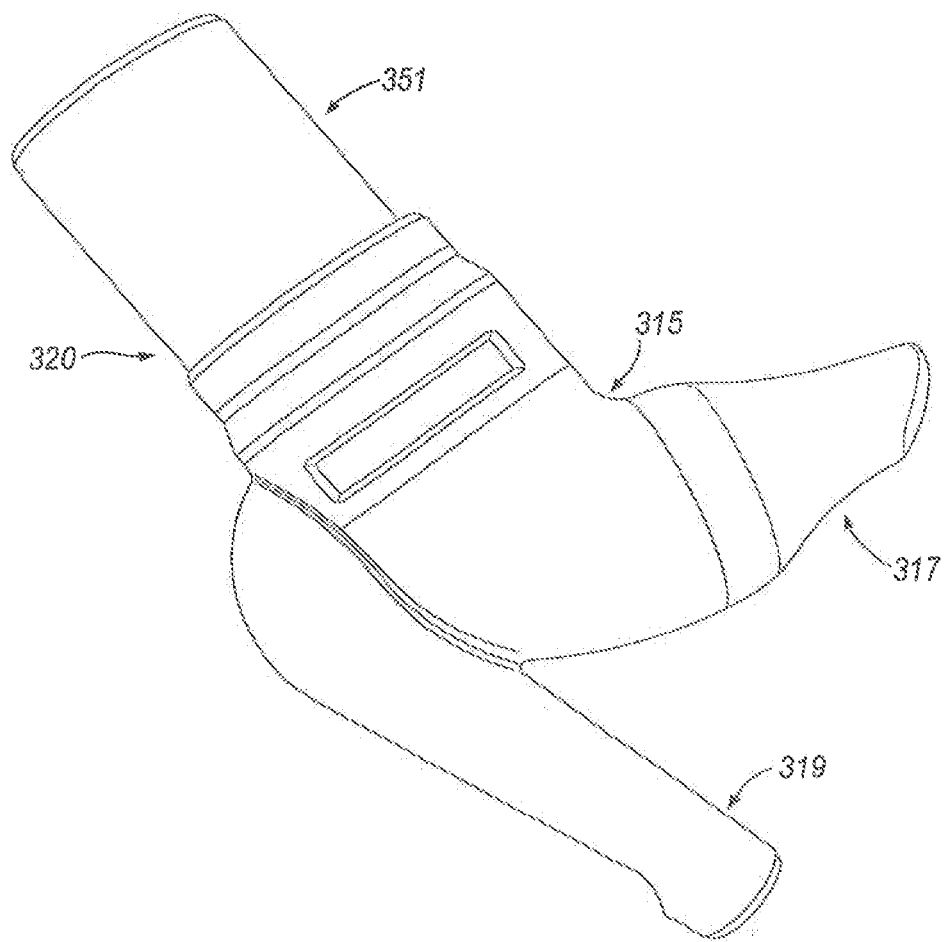
FIGS. 26 and 27 illustrate a nasal delivery device in accordance with an eighth embodiment of the present invention.
Figure 27:
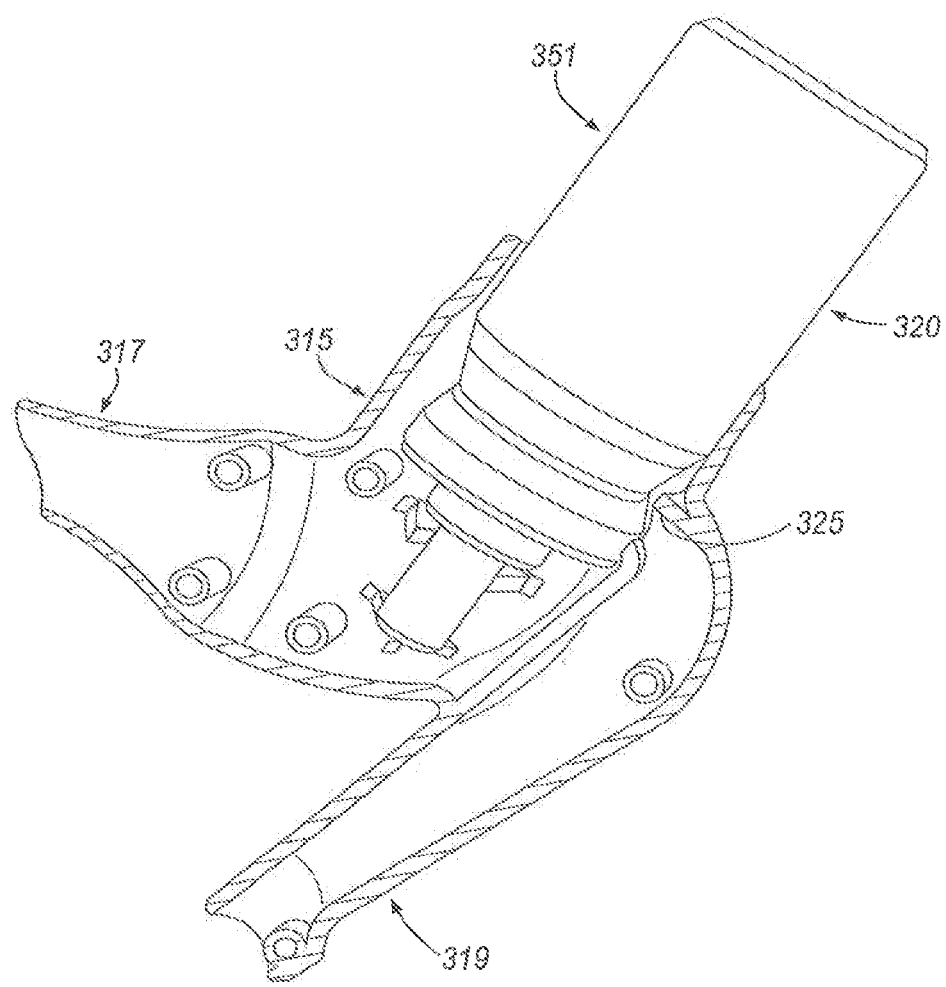
Figure 28:
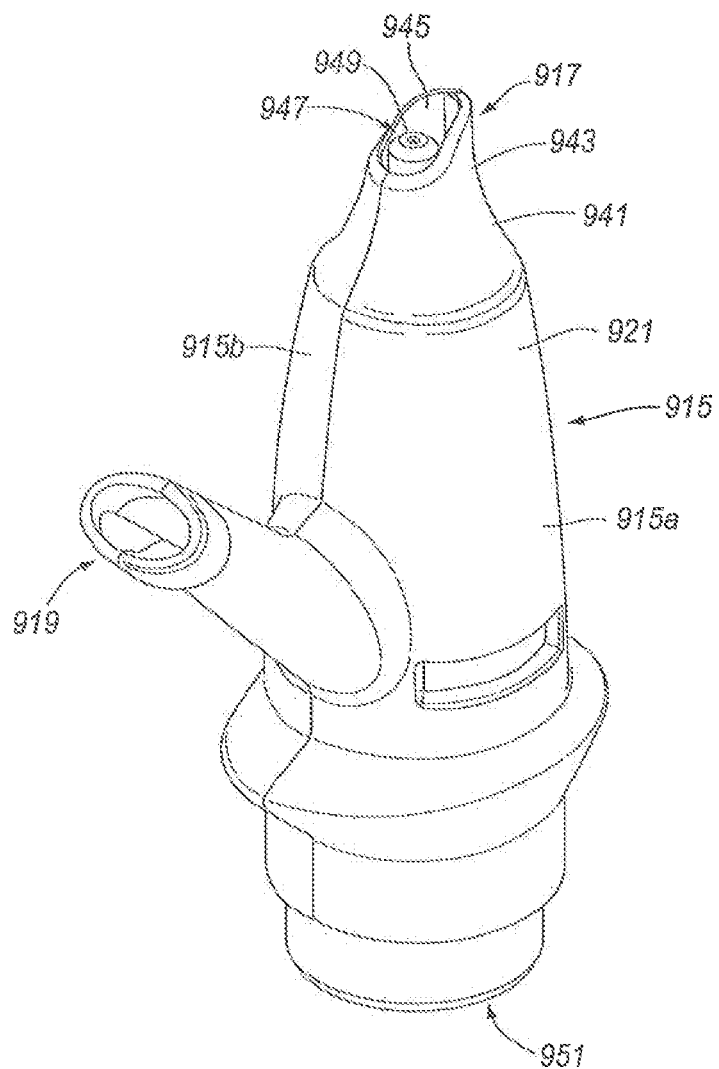
FIGS. 28 to 31 illustrate a nasal delivery device in accordance with a ninth embodiment of the present invention.
Figure 29:
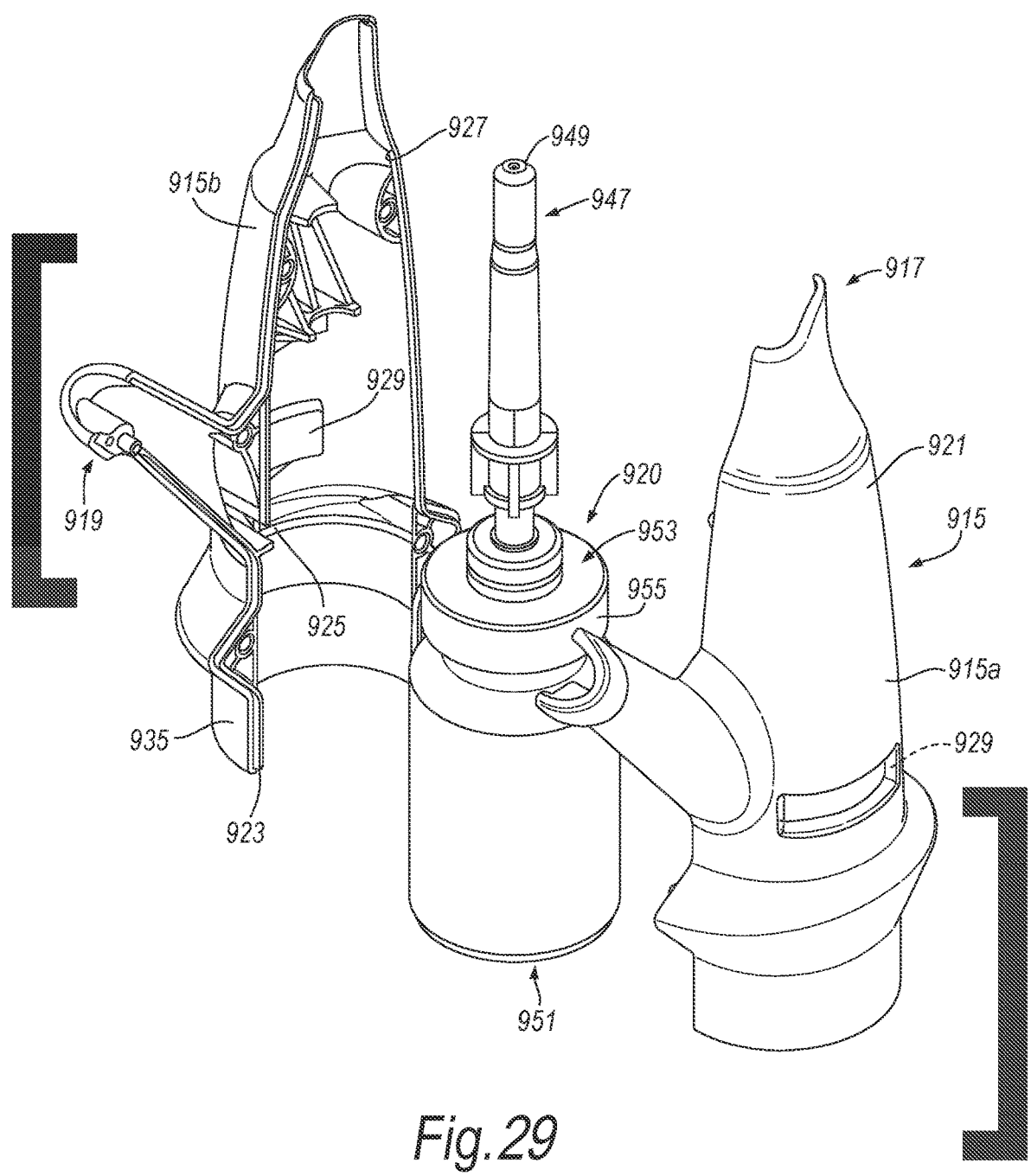

FIGS. 26 and 27 illustrate a manually-actuated nasal delivery device in accordance with an eighth embodiment of the present invention.

This embodiment is very similar to the fourth-described embodiment, and thus, in order to avoid unnecessary duplication of description, only the differences will be described in detail, with like reference signs designating like reference parts.

This embodiment differs principally in the configuration of the nosepiece 317 and the mouthpiece 319, and is configured particularly for use of a pMDI as the substance supply unit 320, with the valve stem of the pMDI being downwardly directed.

In this embodiment the pMDI is actuated by manual downward depression of the base of the canister. In an alternative embodiment the device could include a side-actuating mechanism, which provides for actuation of the pMDI through application of a lateral actuating force relative to the axis of substance delivery. This mechanism can, for example, take the form of one or more pivoted elements which, when depressed laterally, bias the canister downwardly. In one embodiment the pivoted element could provide a cap which protects the nosepiece 317 and/or the mouthpiece 319 in the closed configuration and be moved to an operative position to allow for actuation of the substance supply unit 320.

FIGS. 28 to 31 illustrate a manually-actuated nasal delivery device in accordance with a ninth embodiment of the present invention.

The delivery device comprises a housing 915, in this embodiment formed from two half shells 915a, 915b, a nosepiece 917 for fitting in a nasal cavity of a subject, a mouthpiece 919 into which the subject in use exhales, such as to enable delivery of an air flow into and through the nasal airway of the subject on exhalation by the subject through the mouthpiece 919, and a substance supply unit 920, which is manually operable to deliver substance to the nasal cavity of the subject.

The housing 915 comprises a body member 921, in this embodiment of elongate, tubular section, which receives the substance supply unit 920 and includes an aperture 923 at one end thereof, through which projects an actuating part of the substance supply unit 920, in this embodiment as defined by a base of a substance-containing chamber 951.

The body member 921 further includes an inlet 925 which is in fluid communication with the mouthpiece 919, and an outlet 927 which is in fluid communication with the nosepiece 917.

In this embodiment the body member 921 further includes at least one, here first and second guides 929, 929 on an inner peripheral surface thereof, which act to fix the position of the substance supply unit 920, here by engagement with a body part 955 thereof, when in the inoperative position, such as to ensure that the inlet 925 is closed by the substance supply unit 920 when in the inoperative position.

In this embodiment the body member 921 includes a tubular section 935 which provides substantially for a sealing fit with the substance-containing chamber 951 and thereby prevents the escape of an exhalation air flow through the actuating aperture 923.

The nosepiece 917 comprises a body member 941 which defines an outer sealing surface 943 for providing a sealing fit between the nosepiece 917 and a nasal cavity of the subject, and an inner delivery channel 945, which is in selective fluid communication with the mouthpiece 919 such that an air flow is selectively delivered into and through the nasal airway of the subject on exhalation by the subject through the mouthpiece 919, and an outlet unit 947 for delivering substance into the nasal airway of the subject, which is disposed within the delivery channel 945.

In this embodiment the outlet unit 947 comprises a nozzle 949 for delivering substance to the nasal airway of the subject. In this embodiment the nozzle 949 is disposed in the delivery channel 945 co-axially with the same. In this embodiment the nozzle 949 is configured to provide an aerosol spray. In an alternative embodiment, for the delivery of a liquid, the nozzle 949 could be configured to deliver a liquid jet as a column of liquid.

In a preferred embodiment the distal end of the outlet unit 947 is configured to extend at least about 2 cm, preferably at least about 3 cm, and more preferably from about 2 cm to about 3 cm, into the nasal cavity of the subject.

Figure 30:
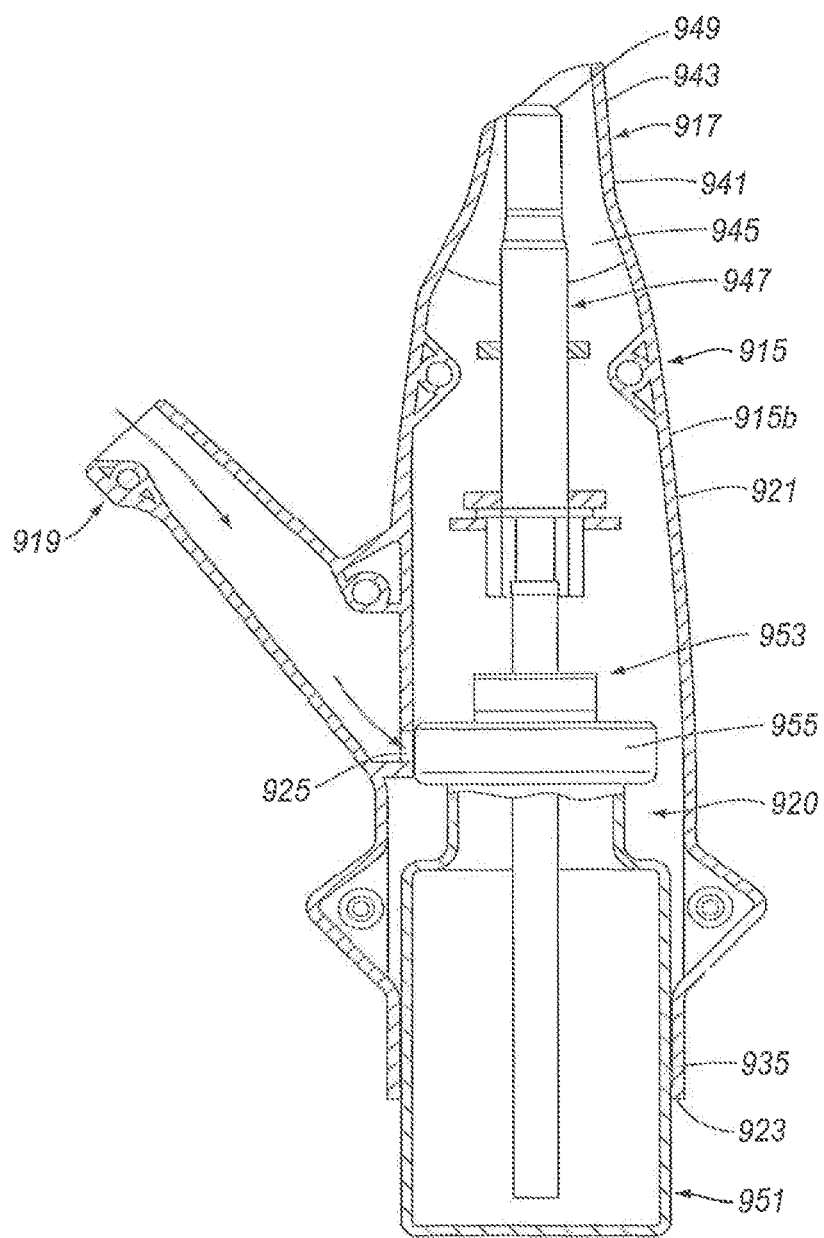
Figure 31:
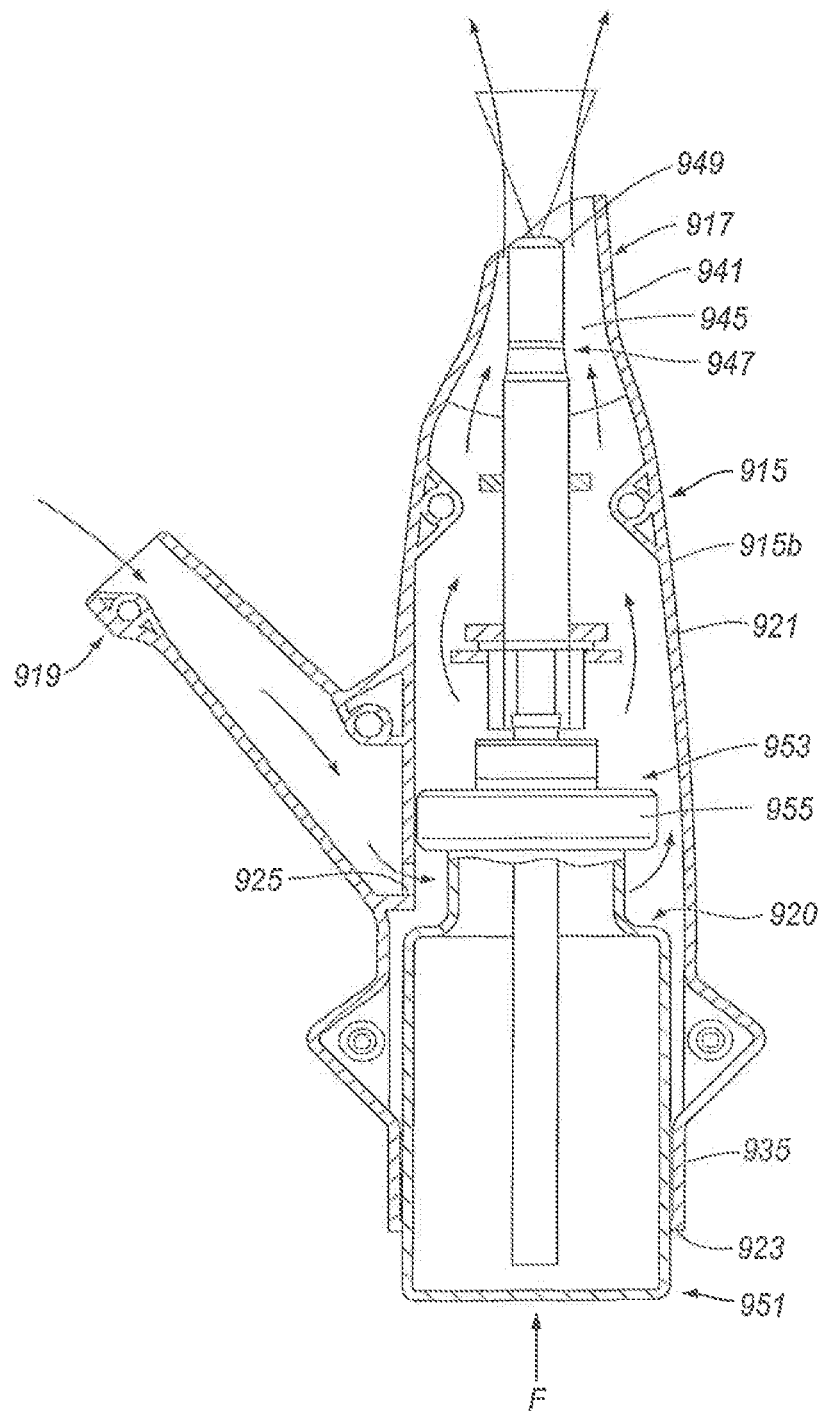

In this embodiment the substance supply unit 920 is a pump unit, which comprises a substance-containing chamber 951 which contains substance and extends from the aperture 923 in the housing 915 as the actuating part of the substance supply unit 920, and a mechanical delivery pump 953 which is actuatable, here by depression of the substance-containing chamber 951 from an inoperative position, as illustrated in FIG. 30, to an actuated position, as illustrated in FIG. 31, such as to deliver a metered dose of substance from the substance-containing chamber 951 to the outlet unit 947 and from the nozzle outlet 949 thereof, here as an aerosol spray.

In this embodiment the substance-containing chamber 951 includes a body part 955, here a head part, typically a ferrule, which is configured such as to close the inlet 925 of the body member 921 when the substance supply unit 920 is in the inoperative or rest configuration, with the position of the body part 955 being located by the guides 929, 929, as illustrated in FIG. 30, such as to prevent the delivery of an air flow through the nosepiece 917 on exhalation by the subject into the mouthpiece 919, and open the inlet 925 of the body member 921 when the substance supply unit 920 is in the actuated configuration, as illustrated in FIG. 31, such as to provide for an air flow, in this embodiment in the form of a burst of air, through the nosepiece 917 simultaneously with actuation of the substance supply unit 920.

In this embodiment the mechanical delivery pump 953 is a liquid delivery pump for delivering a metered dose of substance, but in an alternative embodiment the mechanical delivery pump 953 could be a powder delivery pump, which delivers metered doses of a powdered substance on actuation thereof.

In this embodiment the substance supply unit 920 is a multi-dose unit for delivering a plurality of metered doses of substance in successive delivery operations.

In an alternative embodiment the substance supply unit 920 could be a single-dose unit for delivering a single metered dose of substance or a duo-dose unit for delivering two metered doses of substance in two successive delivery operations.

In another alternative embodiment the substance supply unit 920 could comprise a dry powder delivery unit which delivers metered doses of a substance, as a dry powder, on actuation thereof.

In yet another alternative embodiment the substance supply unit 920 could comprise a nebulizer which delivers metered doses of a substance, as an aerosol spray, on actuation thereof.

In still another alternative embodiment the substance supply unit 920 could comprise an aerosol canister for delivering metered volumes of a propellant, preferably a hydrofluoroalkane (HFA) propellant or the like, containing substance, either as a suspension or solution.

Figure 32:
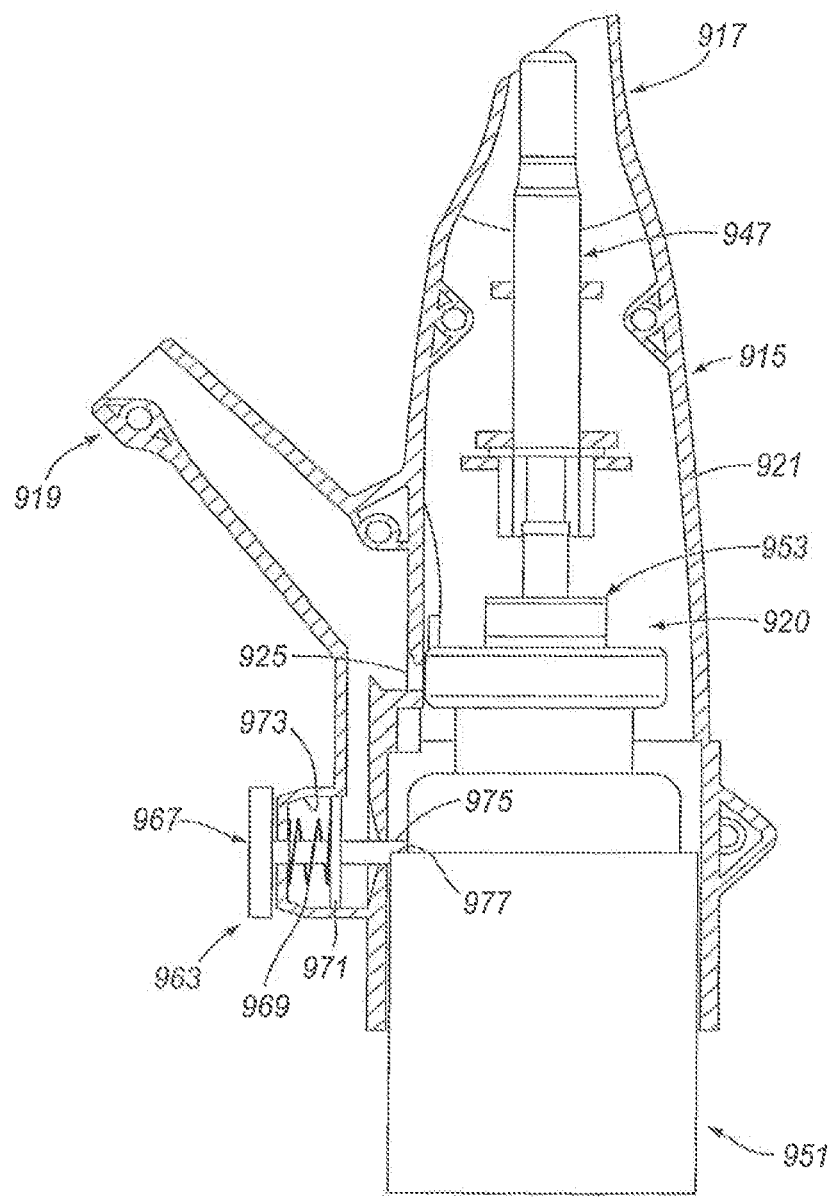
FIGS. 32 and 33 illustrate a nasal delivery device in accordance with a tenth embodiment of the present invention.
Figure 33:
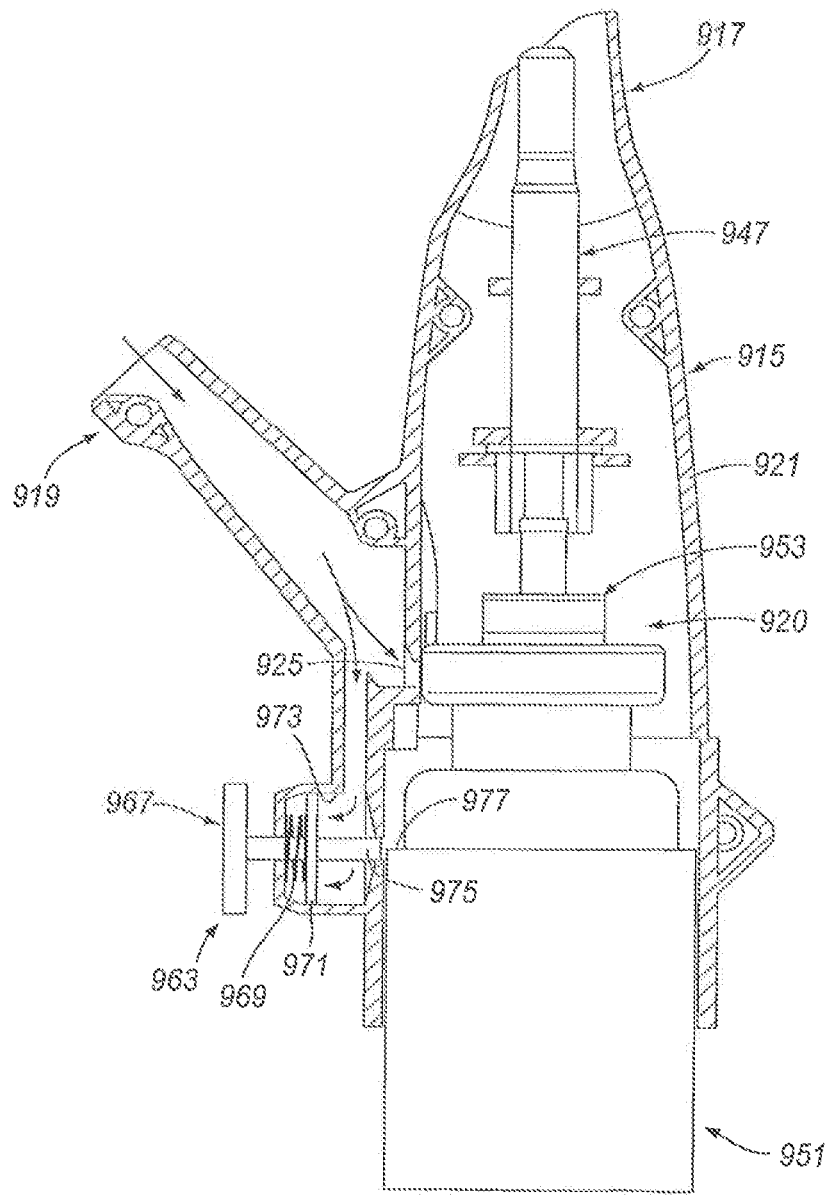

FIGS. 32 and 33 illustrate a manually-actuated nasal delivery device in accordance with a tenth embodiment of the present invention.

This embodiment is very similar to the ninth-described embodiment, and thus, in order to avoid unnecessary duplication of description, only the differences will be described in detail, with like reference signs designating like reference parts.

This embodiment differs in further comprising a latch mechanism 963, which is operable between a closed, inoperative configuration, as illustrated in FIG. 32, in which the device is inoperative, and an open, operative configuration, as illustrated in FIG. 33, in which the substance supply unit 920 is actuatable.

The latch mechanism 963 comprises a latch member 967 which is movably coupled, in this embodiment slideably-coupled, to the body member 921, and a biasing element 969, in this embodiment a resilient element, which acts to bias the latch member 967 to a closed, inoperative position, in this embodiment an inner position, as illustrated in FIG. 32, with the latch mechanism 963 being operated by the exhalation breath of the subject to move the latch member 967 to an open, operative position, in this embodiment an outer position, against the bias of the biasing element 969, as illustrated in FIG. 33, which permits actuation of the substance supply unit 920.

In this embodiment the latch member 967 comprises a piston element 971 which is slideably disposed in a piston bore 973 which is fluidly connected to the mouthpiece 919, such that an exhalation pressure acts on the piston element 971 to move the latch member 967 to the operative position against the bias of the biasing element 969, and a detent 975 which acts to engage a counterpart detent 977 of the substance supply unit 920 and prevent actuation of the same when the latch member 967 is in the closed position, and is moved out of engagement with the counterpart detent 977 of the substance supply unit 920 to allow actuation of the same when the latch member 967 is in the operative position.

With this configuration, for so long as the subject is exhaling through the mouthpiece 919 sufficiently to displace the latch member 967 to the open position, the substance supply unit 920 is actuatable.

In this embodiment the latch mechanism 963 is configured such as to require the generation of a predetermined pressure at the mouthpiece 919 to move the latch member 967 to the operative position. In this way, inadvertent actuation is prevented and closure of the velum of the subject is ensured prior to actuation of the substance supply unit 920.

Figure 34:
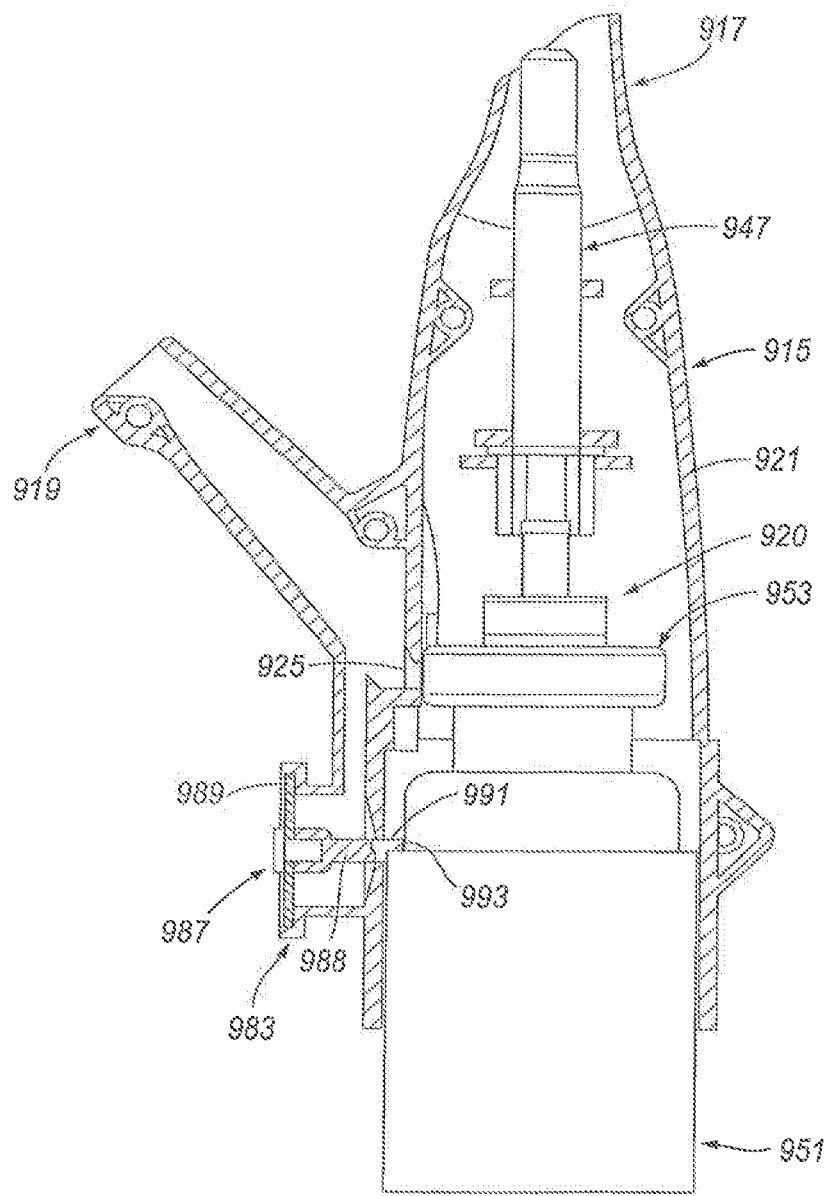
FIGS. 34 and 35 illustrate a nasal delivery device in accordance with an eleventh embodiment of the present invention.
Figure 35:
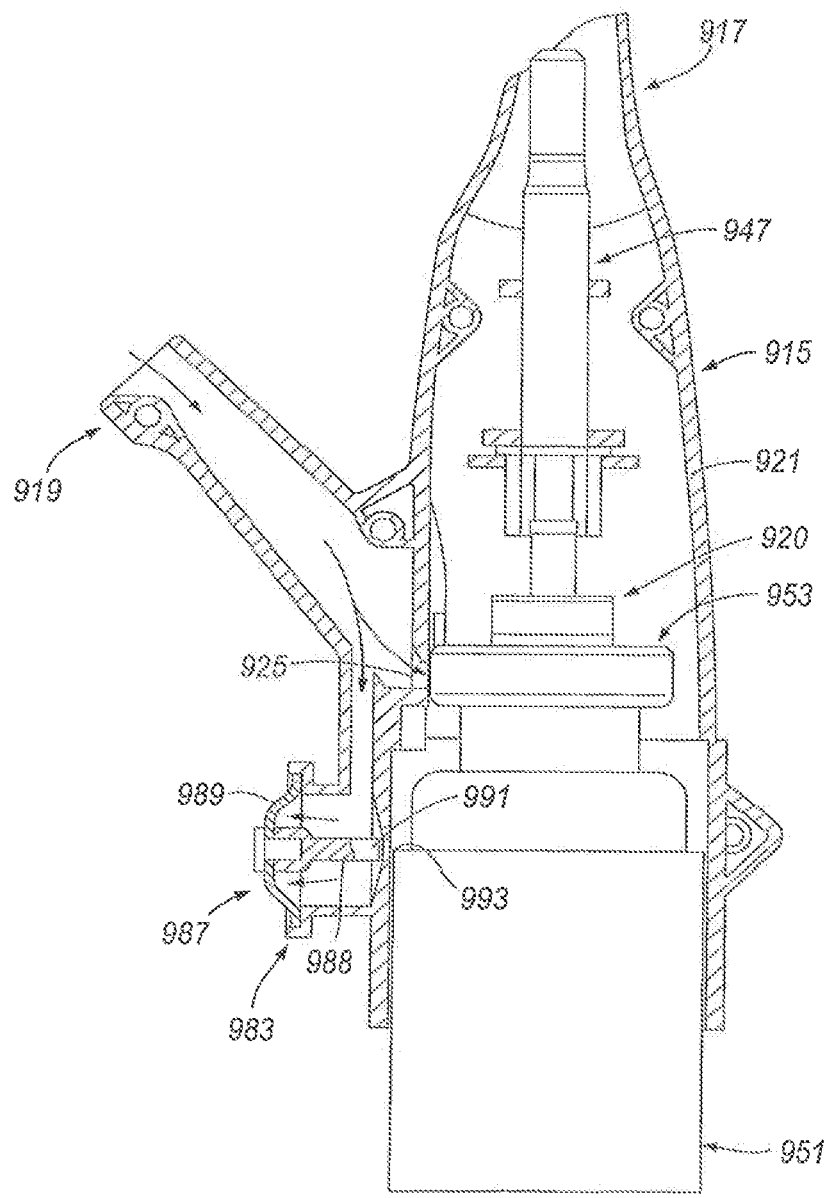

FIGS. 34 and 35 illustrate a manually-actuated nasal delivery device in accordance with an eleventh embodiment of the present invention.

This embodiment is very similar to the ninth-described embodiment, and thus, in order to avoid unnecessary duplication of description, only the differences will be described in detail, with like reference signs designating like reference parts.

This embodiment differs in further comprising a latch mechanism 983, which is operable between a closed, inoperative configuration, as illustrated in FIG. 34, in which the device is inoperative, and an open, operative configuration, as illustrated in FIG. 35, in which the substance supply unit 920 is actuatable.

The latch mechanism 983 comprises a latch member 987 which is movably coupled, in this embodiment flexibly-coupled, to the body member 921, and comprises a latch element 988 and a flexible element 989, in this embodiment in the form of a resilient element, here a diaphragm, which supports the latch element 988 and is fluidly connected to the mouthpiece 919, with the flexible element 989 acting to bias the latch element 988 to a closed, inoperative position, in this embodiment an inner position, as illustrated in FIG. 34, and the latch mechanism 983 being operated by the exhalation breath of the subject to move the latch element 988 to an open, operative position, in this embodiment an outer position, against the bias of the flexible element 989, as illustrated in FIG. 35, which permits actuation of the substance supply unit 920.

In this embodiment the latch element 988 includes a detent 991 which acts to engage a counterpart detent 993 of the substance supply unit 920 and prevent actuation of the same when the latch member 987 is in the closed position, and is moved out of engagement with the counterpart detent 993 of the substance supply unit 920 to allow actuation of the same when the latch member 987 is in the operative position.

With this configuration, for so long as the subject is exhaling through the mouthpiece 919 sufficiently to displace the latch member 987 to the open position, the substance supply unit 920 is actuatable.

In this embodiment the latch mechanism 983 is configured such as to require the generation of a predetermined pressure at the mouthpiece 919 to move the latch member 987 to the operative position. In this way, inadvertent actuation is prevented and closure of the velum of the subject is ensured prior to actuation of the substance supply unit 920.

The nasal delivery devices of the present invention provides for delivery to the olfactory region, which region is located in the superior region of the nasal cavities and represents the only region where it is possible to circumvent the blood-to-brain barrier (BBB) and enable communication with the cerebrospinal fluid (CSF) and the brain.

The substances delivery by the nasal delivery devices include:

Angiotensin antagonists;

Angiotensin (AT) II receptor antagonists, also known as angiotensin receptor blockers, AT1 receptor antagonists and sartans, which include losartan (sold as Cozaar® by Merck & Co);

Angiotensin-converting enzyme (ACE) inhibitors;

Glycine receptor antagonists;

Anti-histamines, in particular non-selective antihistamines, such as dimebon (2,3,4,5-tetrahydro-2,8-dimethyl-5-[2-(6-methyl 3-pyridinypethyl]-1H-pyrido[4,3-b]indole provided as the dichloride salt);

Morphine;

Glycogen synthase kinase 3 (GSK3) inhibitors, including substituted pyrazolo[3,4-b]pyridin-6-ones as disclosed in U.S. Pat. Nos. 7,300,943 and 7,300,944, the contents of which are herein incorporated by reference, substituted 4-amino[1,2,4]triazolo[4,3-a]quinoxalines as disclosed in U.S. Pat. No. 7,202,245, the content of which is herein incorporated by reference, pyrimidine and pyridine derivatives as disclosed in U.S. Pat. Nos. 6,417,185, 6,489,344, 7,037,918, 7,045,519 and US-2006/0089369, the contents of which are herein incorporated by reference, and lithium; Tumor necrosis factor (TNF) blockers, including etanercept (sold as ENBREL® by Wyeth), infliximab (sold as REMICADE® by Centocor, Inc.) and adalimumab (sold as HUMIRA® by Abbott Laboratories);

Oxytocin for the treatment of neurological diseases and conditions, including neurodegenerative diseases and conditions, including Alzheimer's disease, Huntington's disease, Parkinson's disease, dementia and stroke, bi-polar disorder, diabetes, schizophrenia, depression, anxiety, hair loss, cancer, obesity, atherosclerotic cardiovascular disease, essential hypertension, polycystic ovary syndrome, syndrome X, ischemia, especially cerebral ischemia, traumatic brain injury, immunodeficiency, autism, sexual dysfunction, regulation of maternal behaviour, regulation of female sexual behaviour, regulation of male sexual behaviour, regulation of social behaviour, including regulation of male and female aggression, promoting social memory, including social recognition and pair bonding, promoting learning, promoting memory, suppression of fever, and by way of pain relief, such as in the treatment of breakthrough pain, for example, in cancer patients.

Finally, it will be understood that the present invention has been described in its preferred embodiments and can be modified in many different ways without departing from the scope of the invention as defined by the appended claims.

In one alternative embodiment the mouthpiece of the above-described devices can be movable, either through a flexible or hinged connection, such as to allow the relationship between the mouthpiece and the nosepiece to be adjusted, in terms of angle, rotational position and length, in dependence of the anatomy of the subject.

In other embodiments the above-described devices can be modified so as to be configurable to a collapsed or folded configuration, and these embodiments can be configured such as to be locked in the collapsed or folded configuration and thereby prevent accidental or unintentional actuation. These embodiments can also be configured to close the mouthpiece in the folded or collapsed configuration, such as to prevent the entry of foreign matter into the devices.

In preferred embodiments the delivery devices are configured to deliver substance through one nostril of a subject at such a pressure as to flow around the posterior margin of the nasal septum and out of the other nostril of the subject, thereby achieving bi-directional delivery through the nasal cavities as disclosed in WO-A-2000/051672. In alternative embodiments the delivery device could be configured to deliver substance at a reduced pressure which is not sufficient to achieve bi-directional delivery through the nasal cavities. Such embodiments are still advantageous as compared to known delivery devices in providing for velum closure and being capable of achieving targeted delivery, particularly when certain regions of the nasal cavity are obstructed by cuff members.

In another embodiment the present invention allows for re-constitution of the substance to be delivered, for example, in the re-constitution of drug products at point-of-care settings. The substance components can be liquid/liquid, powder/liquid or powder/powder. Typical applications include the re-constitution of lyophilized drug products.

Figure 36:
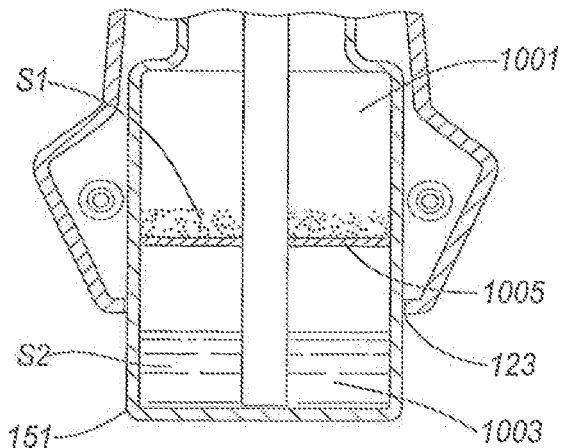
FIGS. 36 and 37 illustrate one embodiment of the present invention as a modification of the second-described embodiment.
Figure 37:
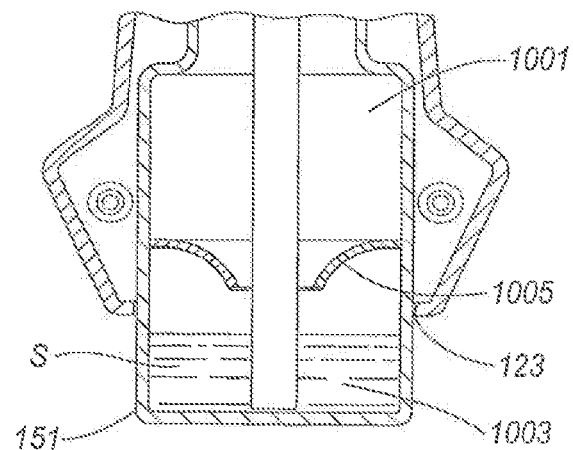

FIGS. 36 and 37 illustrate one embodiment, as a modification of the second-described embodiment, in which the substance-containing chamber 151 comprises first and second chambers 1001, 1003 which each contain a respective substance component S1, S2, and a frangible member 1005, here in the form of a membrane, which normally separates the first and second chambers 1001, 1003, as illustrated in FIG. 36, and when broken allows for re-constitution of the substance components S1, S2 to provide a re-constituted substance S, as illustrated in FIG. 37, for delivery by the delivery device.

In this embodiment the frangible member 1005 is configured to be broken by application of a sudden shock to the substance-containing chamber 151. In an alternative embodiment one of the first and second chambers 1001, 1003 could include a loose element which is configured to rupture the frangible member 1005 on shaking the substance-containing chamber 151.

FIGS. 38 and 39 illustrate another embodiment, again as a modification of the second-described embodiment, in which the substance-containing chamber 151 comprises first and second chambers 1011, 1013 which each contain a respective substance component S1, S2, and a frangible member 1015, here in the form of a membrane, which normally separates the first and second chambers 1011, 1013, as illustrated in FIG. 38, and when broken allows for re-constitution of the substance components S1, S2 to provide a re-constituted substance S, as illustrated in FIG. 39, for delivery by the delivery device.

In this embodiment the housing 115 includes a rupturing element 1021 which is configured to rupture the frangible member 1015 on fitting the substance-containing chamber 151 to the housing 115. In an alternative embodiment the rupturing element 1021 could be provided by part of the delivery pump 153 to which the substance-containing chamber 151 is fitted, in one embodiment the dip tube of the delivery pump 153.

In an alternative embodiment the rupturing element 1021 could be provided by a manually-actuable element, such as a button, which is manually operated to rupture the frangible member 1015. In one embodiment the manually-actuable element can be configured to be operated prior to fitting of the substance-containing chamber 151. In another embodiment the manually-actuable element can be configured to be operated when the substance-containing chamber 151 is fitted in the housing 115.

It will be understood that, although these embodiments relating to the re-constitution of the delivered substance have been described as modifications of the above-described second embodiment, the described modifications have equal application to the other-described embodiments.

In another modification, the delivery devices can include an indicator, such as an audible, tactile or visual indicator, for example, a whistle or pop-up balloon, for providing an indication of the establishment of a suitable pressure at the mouthpiece 19, 119, 219, 319, 419, 519, 619, 919 prior to actuation of the devices.

In a further modification, the delivery devices can include an indicator, such as an audible, tactile or visual indicator, for example, a whistle or pop-up balloon, for providing an indication following actuation of the devices.

In a yet further modification, the delivery devices could include a breath-actuated flow regulator.

In the above-described embodiments the nosepiece 17, 117, 217, 317, 417, 517, 617, 917 has a tapered, asymmetrical configuration. Other symmetrical configurations could equally be employed, for example, tips of oval or circular shape.

A particular advantage of symmetrical configurations is that the delivery device can be used in an orient which allows the mouthpiece 19, 119, 219, 319, 419, 519, 619, 919 to be exposed and an air flow delivered by another person, typically through a tube attached to the mouthpiece 19, 119, 219, 319, 419, 519, 619, 919 with a virus and bacterial filter. This functionality allows for use with unconscious or uncooperative subjects, such as subjects with trauma, for example, subjects involved in accidents or suffering from epilepsy.

Another advantage of symmetrical configurations is that the nosepiece 17, 117, 217, 317, 417, 517, 617, 917 can be rotated to allow for the length and configuration of the device to be altered in order to accommodate differently-sized noses.

Further, in the above-described embodiments, the tip of the nozzle outlet 47, 147, 247, 347, 447, 547, 647, 947 can be flush or substantially flush with the tip of the nosepiece 17, 117, 217, 317, 417, 517, 617, 947, such as to facilitate cleaning of the nozzle outlet 47, 147, 247, 347, 447, 547, 647, 947. Some substances can leave deposits at the nozzle outlet 47, 147, 247, 347, 447, 547, 647, 947. Examples include steroid suspensions which leave crystal deposits.

In a still yet further modification, the delivery devices could be modified to include mouthpieces 19, 119, 219, 319, 419, 519, 619, 919 in the form of flexible tubular elements.

The invention claimed is:

1. A nasal delivery device for delivering a substance to a nasal airway of a subject, comprising:
a housing;
a mouthpiece through which the subject in use exhales to cause closure of the oropharyngeal velum of the subject;
a nosepiece for fitting to a nostril of the subject, wherein the nosepiece includes a nozzle through which the substance is in use delivered as an aerosol spray into the nasal airway of the subject;
a manually-actuatable substance supply unit for delivering the substance through the nozzle, wherein the substance supply unit comprises a substance-containing chamber which contains the substance and extends from an aperture in the housing as an actuating part of the substance supply unit, and a mechanical delivery pump which is actuatable by depression of the substance-containing chamber to deliver the substance from the nozzle; and
a valve assembly which is fluidly connected to the mouthpiece and the nosepiece and operable between a closed configuration substantially blocking a fluid communication path between the mouthpiece and the nosepiece and an open configuration permitting a flow of fluid through the fluid communication path between the mouthpiece and the nosepiece, wherein the substance-containing chamber is coupled to the valve assembly and configured to provide for simultaneous actuation of the mechanical delivery pump and opening of the valve assembly to deliver an air flow through the fluid communication path simultaneously with delivery of the substance through the nosepiece and to the nasal airway of the subject, wherein the air flow includes a higher pressure or volume when the valve assembly is initially opened compared to a steady state pressure or volume of the air flow after the valve assembly is opened for a predetermined time.

2. The delivery device of claim 1, wherein the substance is a liquid substance.

3. The delivery device of claim 1, wherein the nosepiece includes a sealing member which provides for a tight sealing fit with the nostril of the subject.

4. The delivery device of claim 1, wherein the housing includes an inwardly-tapering section which is downstream of the valve assembly and fluidly connected to the nosepiece.

5. The delivery device of claim 1, wherein the nozzle is disposed co-axially with a delivery channel of the nosepiece.

6. The delivery device of claim 1, wherein the substance supply unit is configured to deliver a metered dose of the substance in a delivery operation.

7. The delivery device of claim 1, wherein the substance supply unit is a multi-dose unit which is configured to deliver a plurality of metered doses of the substance in successive delivery operations.

8. The nasal delivery device of claim 1, wherein delivery of the substance is intended to treat allergic or non-allergic nasal inflammation.

9. The nasal delivery device of claim 8, wherein the nasal inflammation is associated with infection.

10. The nasal delivery device of claim 1, wherein delivery of the substance is intended to treat nasal polyps.

11. The nasal delivery device of claim 1, wherein delivery of the substance is intended to treat rhinitis.

12. The nasal delivery device of claim 1, wherein the substance is an anti-histamine, cromoglycate, steroid, antibiotic, decongestant, anti-microbial agent, or pharmaceutical.

13. The nasal delivery device of claim 1, wherein the substance is delivered from the nozzle as an aerosol.

14. The nasal delivery device of claim 1, wherein the mechanical delivery pump is a liquid delivery pump which delivers metered doses of the substance upon actuation.

15. The nasal delivery device of claim 1, wherein the substance is a substance configured to treat allergic or non-allergic nasal inflammation.

16. The nasal delivery device of claim 15, wherein the nasal inflammation is associated with infection.

17. The nasal delivery device of claim 1, wherein the substance is a substance configured to treat nasal polyps.

18. The nasal delivery device of claim 1, wherein the substance is a substance configured to treat rhinitis.

19. A method of delivering a substance to a nasal airway of a subject, comprising:
providing a delivery device which comprises: a housing; a mouthpiece through which the subject exhales; a nosepiece for fitting to a nostril of the subject, wherein the nosepiece includes a nozzle through which the substance is delivered as an aerosol spray into the nasal airway of the subject; a manually-actuatable substance supply unit for delivering the substance through the nozzle, wherein the substance supply unit comprises a substance-containing chamber which contains the substance and extends from an aperture in the housing as an actuating part of the substance supply unit, and a mechanical delivery pump which is actuatable by depression of the substance-containing chamber to deliver the substance from the nozzle; and a valve assembly which is fluidly connected to the mouthpiece and the nosepiece and operable between a closed configuration substantially blocking a fluid communication path between the mouthpiece and the nosepiece and an open configuration permitting a flow of fluid through the fluid communication path between the mouthpiece and the nosepiece, wherein the substance-containing chamber is coupled to the valve assembly and configured to provide for simultaneous actuation of the mechanical delivery pump and opening of the valve assembly to deliver an air flow through the fluid communication path simultaneously with delivery of the substance through the nosepiece and to the nasal airway of the subject;
fitting the nosepiece to the nostril of the subject;
the subject exhaling through the mouthpiece to close the oropharyngeal velum of the subject; and
manually actuating the substance supply unit by depressing the substance-containing chamber to provide simultaneously for delivery of the substance from the nozzle and opening of the valve assembly to provide an air flow, as a burst of air, to the nasal airway of the subject.

20. The method of claim 19, wherein the substance is a liquid substance.

21. The method of claim 19, wherein the nosepiece fitting comprises:
fitting the nosepiece to the nostril of the subject so that the nosepiece is in sealing engagement with the nostril of the subject.

22. The method of claim 19, wherein the housing includes an inwardly-tapering section which is downstream of the valve assembly and fluidly connected to the nosepiece.

23. The method of claim 19, wherein the nozzle is disposed co-axially with a delivery channel of the nosepiece.

24. The method of claim 19, wherein the substance supply unit delivers a metered dose of the substance in a delivery operation.

25. The method of claim 19, wherein the substance supply unit is a multi-dose unit which delivers a plurality of metered doses of the substance in successive delivery operations.

* * * * *